United States Patent [19]
Aihara et al.

[11] Patent Number: 5,310,500
[45] Date of Patent: May 10, 1994

[54] LIQUID CRYSTAL COMPOUNDS

[75] Inventors: Yoshihiko Aihara; Tadaaki Isozaki; Toru Ooide; Noriko Yamakawa, all of Tokyo, Japan

[73] Assignee: Showa Shell Sekiyu Kabushiki Kaisha, Tokyo, Japan

[21] Appl. No.: 894,429

[22] Filed: Jun. 5, 1992

Related U.S. Application Data

[63] Continuation-in-part of Ser. No. 863,317, Apr. 1, 1992, abandoned, which is a continuation of Ser. No. 724,997, Jul. 2, 1991, abandoned.

[30] Foreign Application Priority Data

Jul. 5, 1990 [JP] Japan ................... 2-178336

[51] Int. Cl.$^5$ ................ C09K 19/32; C07C 69/76
[52] U.S. Cl. ................ 252/299.62; 560/80; 560/73
[58] Field of Search ............ 252/299.62; 560/73, 560/80

[56] References Cited

U.S. PATENT DOCUMENTS 4,921,632 5/1990 Nakamura et al. ............. 252/299.1

FOREIGN PATENT DOCUMENTS 339987 11/1989 European Pat. Off. .
341922 11/1989 European Pat. Off. .
264925 10/1990 Japan .
2264918 10/1990 Japan .
344352 2/1991 Japan .

Primary Examiner—Robert L. Stoll
Assistant Examiner—C. Harris
Attorney, Agent, or Firm—Cushman, Darby & Cushman

[57] ABSTRACT

Antiferroelectric liquid crystal compounds are provided which have the formula $$R_1-CO-O-\bigcirc\bigcirc-Y-A-CO-\overset{CF_3}{\underset{*}{CH}}-R_2$$

wherein
$R_1$ represents an alkyl group having 5-18 carbon atoms,
$R_2$ represents an alkyl group having 6-16 carbon atoms,
Y represents a group $$-O\underset{\underset{O}{\parallel}}{C}- \text{ or } -\underset{\underset{O}{\parallel}}{C}O-$$

and
A represents a group $$-\bigcirc- \text{ or } -\bigcirc-\bigcirc-$$

3 Claims, 14 Drawing Sheets

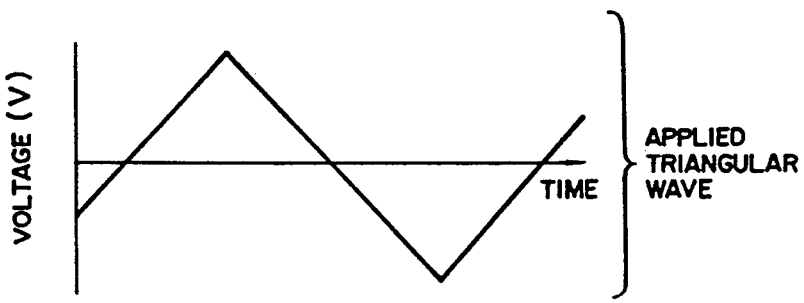
FIG. 4 (A) APPLIED TRIANGULAR WAVE
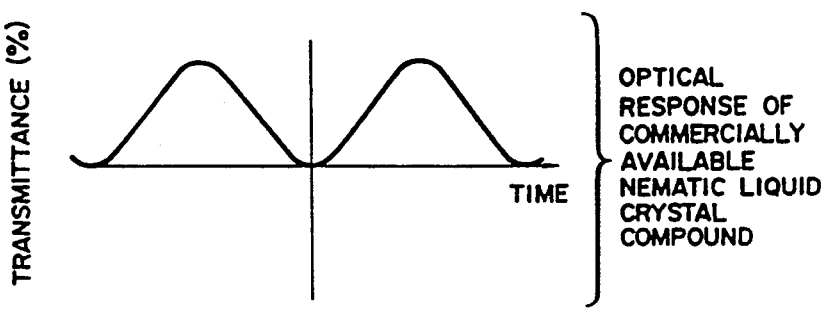
FIG. 4 (B) OPTICAL RESPONSE OF COMMERCIALLY AVAILABLE NEMATIC LIQUID CRYSTAL COMPOUND
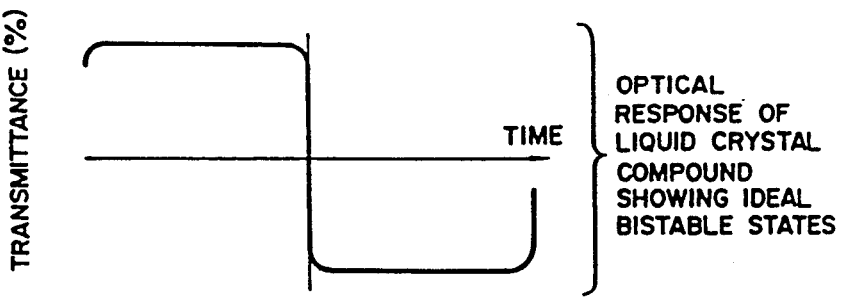
FIG. 4 (C) OPTICAL RESPONSE OF LIQUID CRYSTAL COMPOUND SHOWING IDEAL BISTABLE STATES
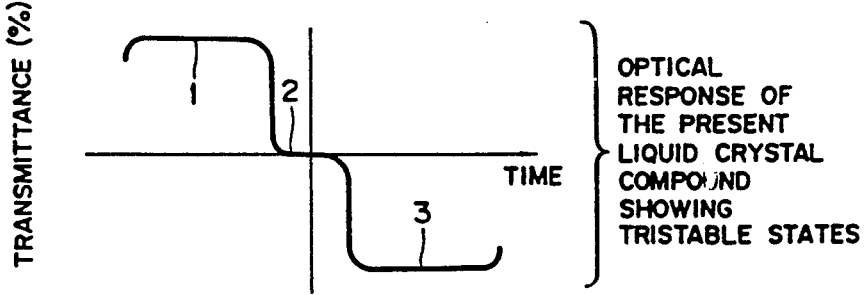
FIG. 4 (D) OPTICAL RESPONSE OF THE PRESENT LIQUID CRYSTAL COMPOUND SHOWING TRISTABLE STATES

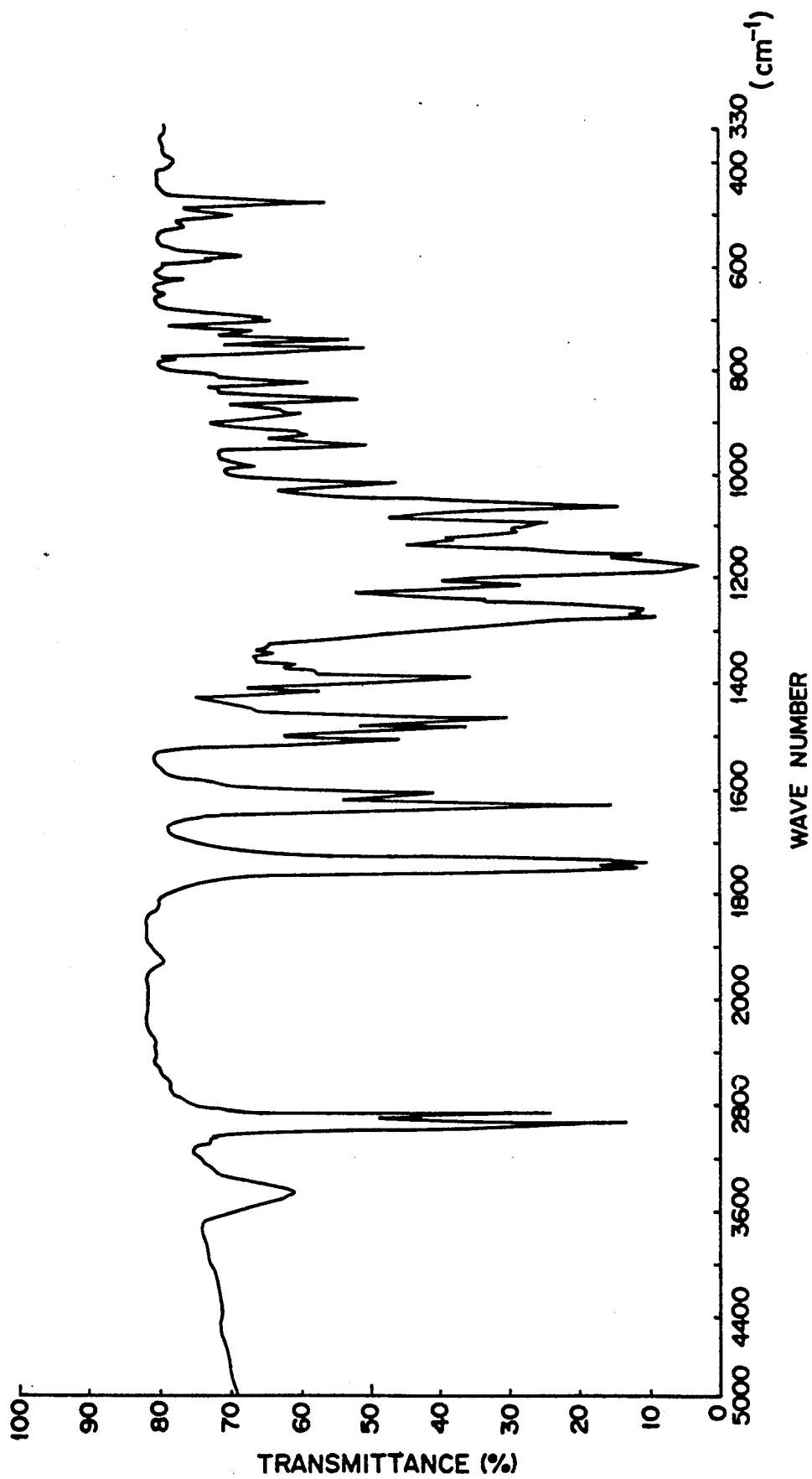

LIQUID CRYSTAL COMPOUNDS

This is a continuation-in-part of the FWC 62 application Ser. No. 07/863,317 filed Apr. 1, 1992, abandoned which is a continuation of Ser. No. 07/724,997 filed Jul. 2, 1991 abandoned.

The present invention is to provide an antiferroelectric liquid crystal compound having a naphthalene skeleton, and the liquid crystal compound relates to liquid crystal compounds used for display devices or electrooptical devices which take advantage of the response to electric field.

Furthermore, the present invention relates to an antiferroelectric liquid crystal compound exhibiting tristable molecular alignments. The liquid crystal compound is used for display devices or electrooptical devices which take advantage of the response to electric field.

As electrooptical devices using nematic liquid crystals such as those of DSM, TN, G-H or STN types have been developed and put to practical use. These electrooptical devices using the nematic liquid crystals have certain drawback suck as a very slow response in the range from several milliseconds to several ten milliseconds and thus are limited in their applications. The slow response of devices utilizing a nematic liquid crystal is attributed to the fact that the weak torque for moving molecules is based on the anisotropy of dielectric constant. Among these backgrounds, a ferroelectric liquid crystal which exhibits spontaneous polarization (Ps) and a strong torque based on Ps x E (E: applied electric field) and is capable of a high speed response in the range of several $\mu$sec to several ten $\mu$sec has been investigated by Meyer et al. (Le Journal de Physique, 36, 1975, L-69). Furthermore, there is disclosed a new antiferroelectric liquid crystal in Japanese Patent Laid-Open Publication No. 307838/1988. There are also the disclosed "tristable states" described later in Japanese Patent Laid-Open Publication Nos. 316339/1989, 316367/1989, 316372/1989 and 28128/1990 by the present applicant.

There have already been proposed several high speed electrooptical devices comprising ferroelectric liquid crystals.

A typical example includes a device in which the helical structure is released by the force of wall faces and the two molecular alignments parallel to the wall faces are changed by the polarity of an applied electric field (see, for example, Japanese Patent Laid-Open Publication No. 107216/1981).

The aforementioned device is composed on the assumption of the presence of a compound which exhibits such an ideal bistable states as is shown by a field response wave pattern in FIG. 1. However, no compound which exhibits such an ideal bistable states as described above has been found, and bistable liquid crystals synthesized hitherto show a field response wave pattern in FIG. 2 but not a field response wave pattern in FIG. 1. It is the present state that if a device which exhibits a response wave pattern as shown in FIG. 2 is intended to be used for a switching circuit of light, such a pattern has a profile that transmittance varies gradually with the variation of an applied voltage from the minus side to the plus side and thus the object cannot be accomplished sufficiently with such a simple change of applied voltage as "on" and "off". Moreover, a bistable state liquid crystal having been synthesized is hard to form a monodomain structure as an ideal molecular alignment in the stage of a S*c phase at no electric field, and it causes disclination (defect) or twist which causes the disturbance of the molecular alignment. It is thus difficult to realize the aforementioned ideal bistable alignment in a large area. Furthermore, it has a low threshold value (voltage at which the brightness varies at a predetermined extent), so that the dynamic drive of it may cause the lowering of contrast or the decrease of the range of viewing angle. The bistable state liquid crystal hitherto synthesized has no memory effect, since it exhibits a hysteresis as shown in FIG. 2. Thus, it is necessary to impress continuously a voltage at $v_3$ in FIG. 2 or to apply a high frequency in order to maintain a stable response in the S*c phase in the liquid crystal, and it cannot avoid a large energy loss.

Eventually, it is the present state that many problems remain unsolved in conventional ferroelectric liquid crystal electrooptical devices notwithstanding the earnest desire of a high speed liquid crystal electrooptical device which takes advantage effectively of an applied field and a bond having a strong molecular alignment obtained in a liquid crystal.

Thus, the object of the present invention is to provide a novel liquid crystal compound which can be used in the liquid crystal electrooptical device described in Japanese Patent Laid-Open Publication No. 153322/1990 and takes advantage of the tristable states, characterized in that the liquid crystal compound realizes a stable molecular alignment having a distinct light-dark contrast depending on applied electric field, generates a sharp threshold and double hysteresis properties as shown in FIG. 3, and realizes easily dynamic drive and is capable of a high speed response.

FIG. 1 shows the hysteresis of an ideal bistable state liquid crystal which has not in fact been obtained, FIG. 2 shows the hysteresis of a practical bistable state liquid crystal having been hitherto synthesized, FIG. 3 shows the hysteresis of tristable state liquid crystal according to the present invention, respectively, in which the abscissa represents applied voltage and the ordinate represents transmittance (%), FIG. 4-A represents a triangular wave voltage applied, and FIGS. 4-B, 4-C and 4-D represent the optical response properties of a commercially available nematic liquid crystal, a bistable state liquid crystal and a tristable state liquid crystal, respectively, and FIGS. 5-12 represent the infrared spectra of the compounds according to the present invention is Examples 1-7 and 9, respectively.

Figure 1:
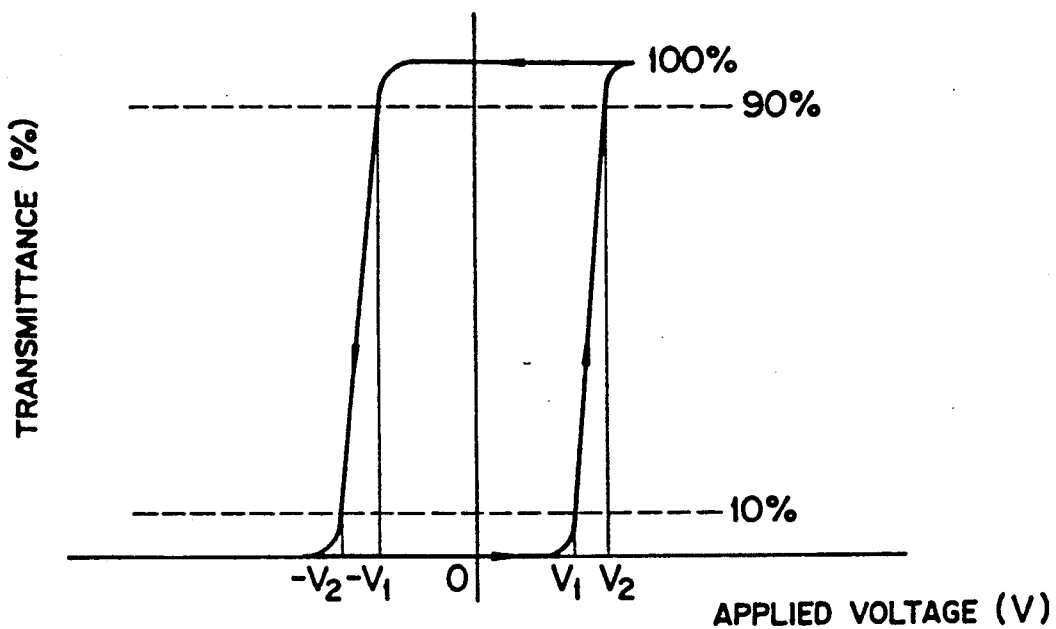
Figure 2:
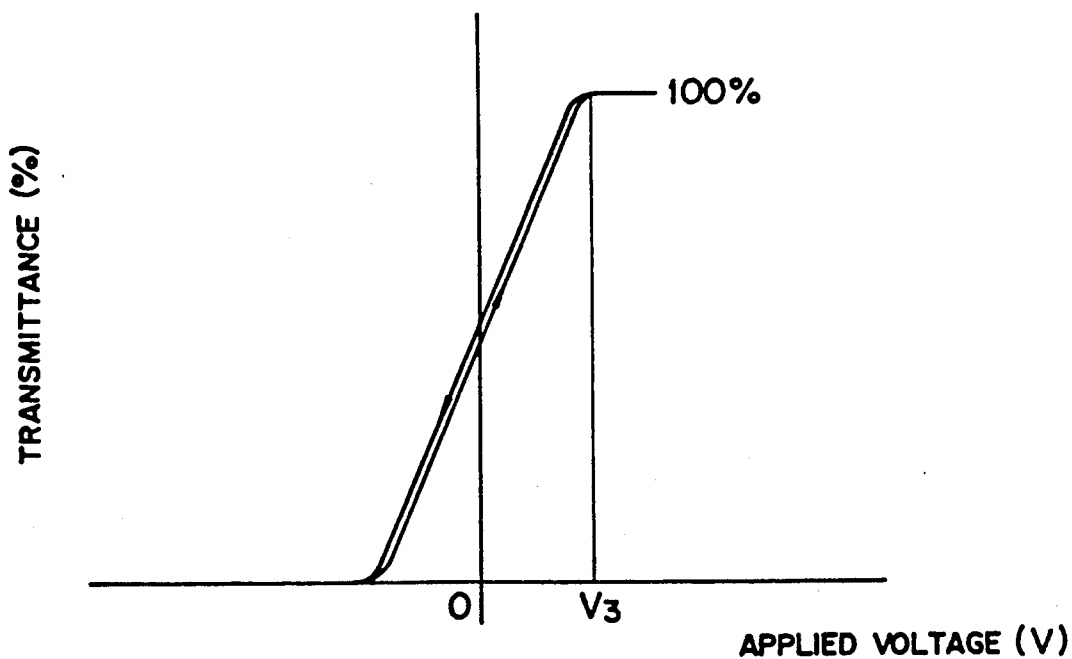
Figure 3:
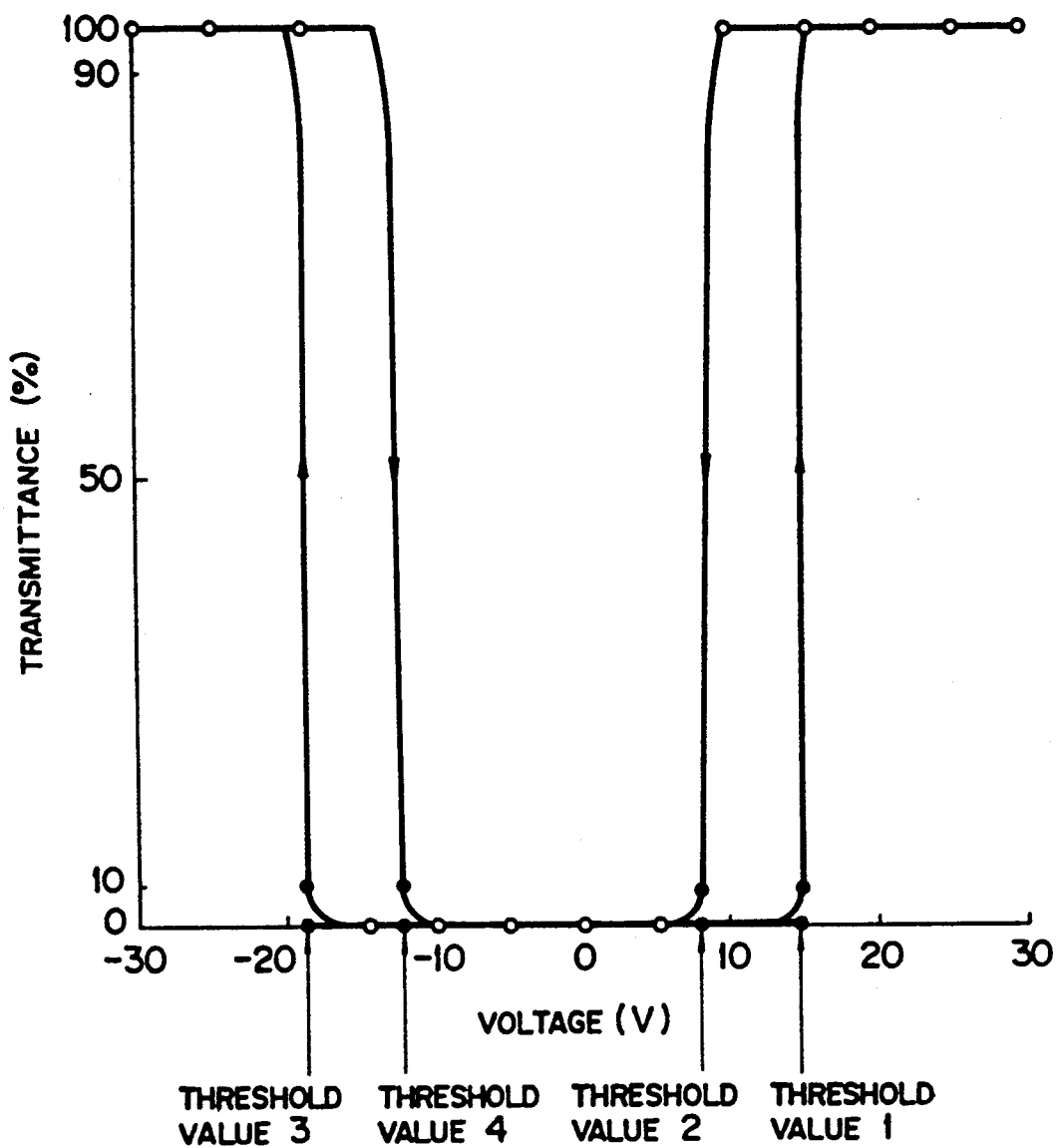

The object of the present invention consists in providing a novel antiferroelectric liquid crystal having new optically tristable states which is distinguished from a ferroelectric liquid crystal exhibiting a chiral smectic phase or a chiral smectic C phase (S*c phase) as the conventional bistable states.

The term "having optically tristable states" means that in a liquid crystal electrooptical device comprising an antiferroelectric liquid crystal inserted between the first electrode plate and the second electrode plate arranged at a predetermined distance from the first electrode plate, characterized in that the device is constituted so that the voltage for forming electric field is applied to the first and second electrode plates, and, on applying the voltage in the shape of a triangular wave as shown in FIG. 4-A, the antiferroelectric liquid crystal has the first stable state of the molecular alignment at no electric field (at 2 in FIG. 4-D), the second stable state different from the first stable state for the one direction of the electric field on applying the electric field (at 1 in FIG. 4-D), and the third stable state different from the first and second stable states for the other direction of the electric field (at 3 in FIG. 4-D). In this connection, the liquid crystal electrooptical device taking advantage of the tristable states has been filed by the present applicants. (Japanese Patent Application No. 70212/1988).

On the other hand, "the commercially available nematic liquid crystal" or the bistable state liquid crystals having been synthesized have not exhibited tristable states but the optical response shown in FIGS. 4-B or C.

The novel tristable state antiferroelectric liquid crystal exhibits an epoch-making effect as a liquid crystal display in comparison with the conventional nematic liquid crystals.

While the conventional liquid crystal having a high image quality is required to take a very complicated structure of the driving mode such as the active matrix mode, the tristable state antiferroelectric liquid crystal is required only a simple display of a matrix type. The conventional type was produced by a complicated process, so that an image plane was difficult to be made in a large size and the production cost was expensive. On the other hand, in the case of the tristable antiferroelectric liquid crystal the production process is simple and epoch-making, so that it is possible to make the image plane in a large size and to control the production cost at an inexpensive level.

The object of the present invention is to provide a novel liquid crystal having the tristable states, i.e., antiferroelectricity.

The present invention first relates to a liquid crystal compound represented by the formula

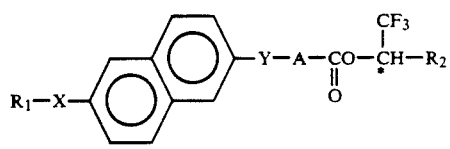

wherein
$R_1$ represents an alkyl group having 5–18 carbon atoms.
$R_2$ represents an alkyl group having 6–16 carbon atoms,
X represents a group —O—,

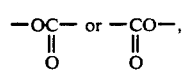

Y represents a group

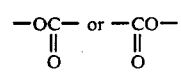

and

A represents a group

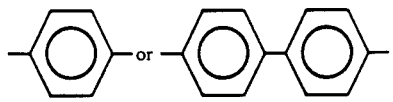

The present invention secondly relates to a liquid crystal compound which is able to exhibit optically tristable states and has the formula (I):

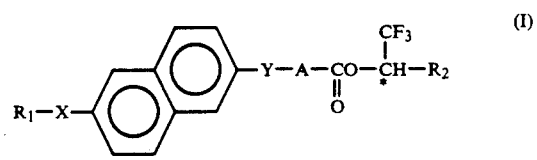

wherein $R_1$, $R_2$, X, Y and A are defined above.

The present invention thirdly relates to a liquid crystal compound which is able to exhibit optically tristable states and has the formula (II):

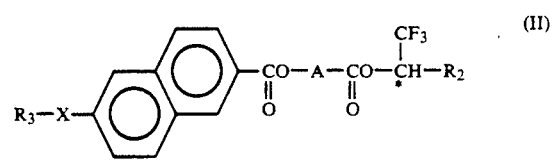

wherein $R_2$ and A are defined above, $R_3$ represents an alkyl group having 6–16 carbon atoms and X represents a group —O— or

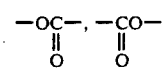

The present invention fourthly relates to a liquid crystal compound which is able to exhibit optically tristable states and has the formula (III):

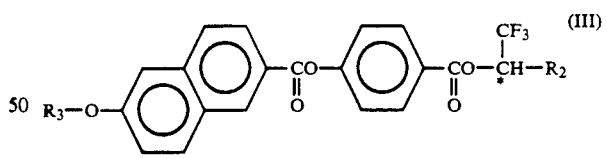

wherein $R_2$ and $R_3$ have the same meanings as above.

The present invention fifthly relates to a liquid crystal compound which is able to exhibit optically tristable states and has the formula (IV):

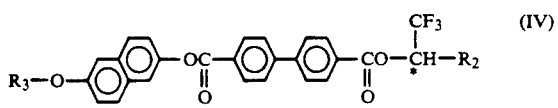

wherein $R_2$ and $R_3$ are defined as above.

The present invention sixthly relates to a liquid crystal compound which is able to exhibit optically tristable states and has the formula (V):

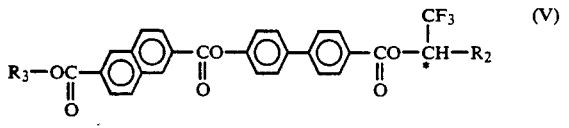 (V)

wherein $R_2$ and $R_3$ are defined above.

The present invention seventhly relates to a liquid crystal compound which is able to exhibit optically tristable states and has the formula (VI):

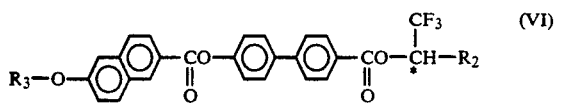 (VI)

wherein $R_2$ and $R_3$ are defined above.

The present invention eightly relates to a liquid crystal compound which is able to exhibit optically tristable states and has the formula (VII):

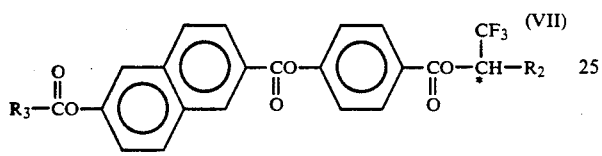 (VII)

wherein $R_2$ and $R_3$ have the same meanings as above.

The present invention ninethly relates to a liquid crystal compound which is able to exhibit optically tristable states and has the formula (VIII):

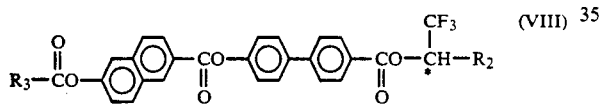 (VIII)

wherein $R_2$ and $R_3$ are defined above.

The six synthetic methods of the compound according to the present invention will be described with reference to respective examples.

(A) 4-Benzyloxybenzoic acid chloride and an optically active 1,1,1-trifluoro-2-alkanol were allowed to react to give 1,1,1-trifluoro-2-alkyl 4-benzyloxybenzoate, which was subjected to hydrogenolysis to give 1,1,1-trifluoro-2-alkyl 4-hydroxybenzoate. An alkyl bromide and 2-hydroxynaphthalene-6-carboxylic acid methyl ester were allowed to react in the presence of potassium carbonate in a solvent such as dimethylformamide and then subjected to hydrolysis with an aqueous sodium hydroxide. The hydrolyzed product was allowed to react with 1,1,1-trifluoro-2-alkyl 4-hydroxybenzoate in the presence of dicyclohexylcarbodiimide to give 6-alkyloxynaphthalene-2-carboxylic acid 4-(1,1,1-trifluoro-2-alkyloxycarbonyl)phenyl ester.

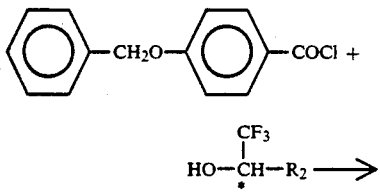

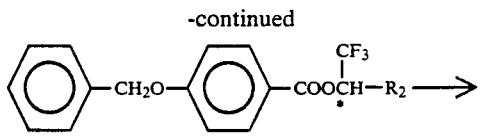

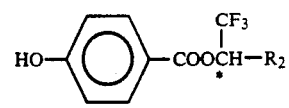

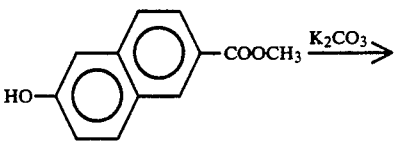

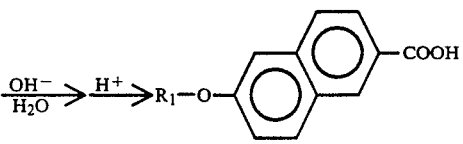

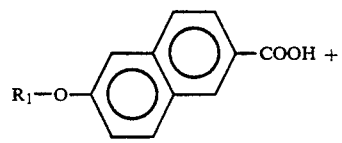

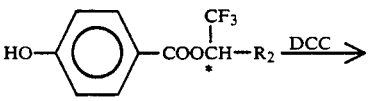

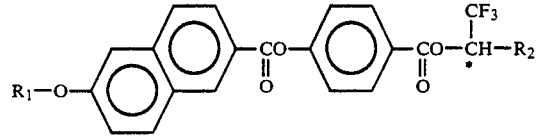

(B) 4-Hydroxybiphenyl-4'-carboxylic acid was dissolved in methanol and heated under refluxing in the presence of concentrated sulfuric acid to give 4-hydroxy-biphenyl-4'-carboxylic acid methyl ester. Then the ester and benzyl bromide were dissolved in a solvent such as DMF and the solution was allowed to react in the presence of anhydrous potassium carbonate to give 4-benzyloxybiphenyl-4'-carboxylic acid methyl ester. The compound obtained was subjected to hydrolysis with an aqueous sodium hydroxide solution to give 4-benzyloxy-biphenyl-4'-carboxylic acid. The compound was further allowed to react with thionyl chloride to give 4-benzyloxy-biphenyl-4'-carboxylic acid chloride.

An optically active 1,1,1-trifluoro-2-alkanol and the aforementioned acid chloride were allowed to react in a solvent such as methylene chloride to give 1,1,1-trifluoro-2-alkyl 4-benzyloxybiphenyl-4'-carboxylate. The ester was subjected to hydrogenolysis to give 1,1,1-trifluoro-2-alkyl 4'-hydroxybiphenyl-4-carboxylate.

An alkyl bromide and 2-hydroxynaphthalene-6-carboxylic acid methyl ester were allowed to react in the presence of potassium carbonate in a solvent such as dimethylformamide and then subjected to hydrolysis with an aqueous sodium hydroxide solution. The hydrolyzed product was allowed to react with the 1,1,1-trifluoro-2-alkyl 4′-hydroxybiphenyl-4-carboxylate in the presence of dicyclohexylcarbodiimide to give 6-alkyloxynaphthalene-2-carboxylic acid 4′-(1,1,1-trifluoro-2-alkyloxycarbonyl)-biphenyl-4-ester.

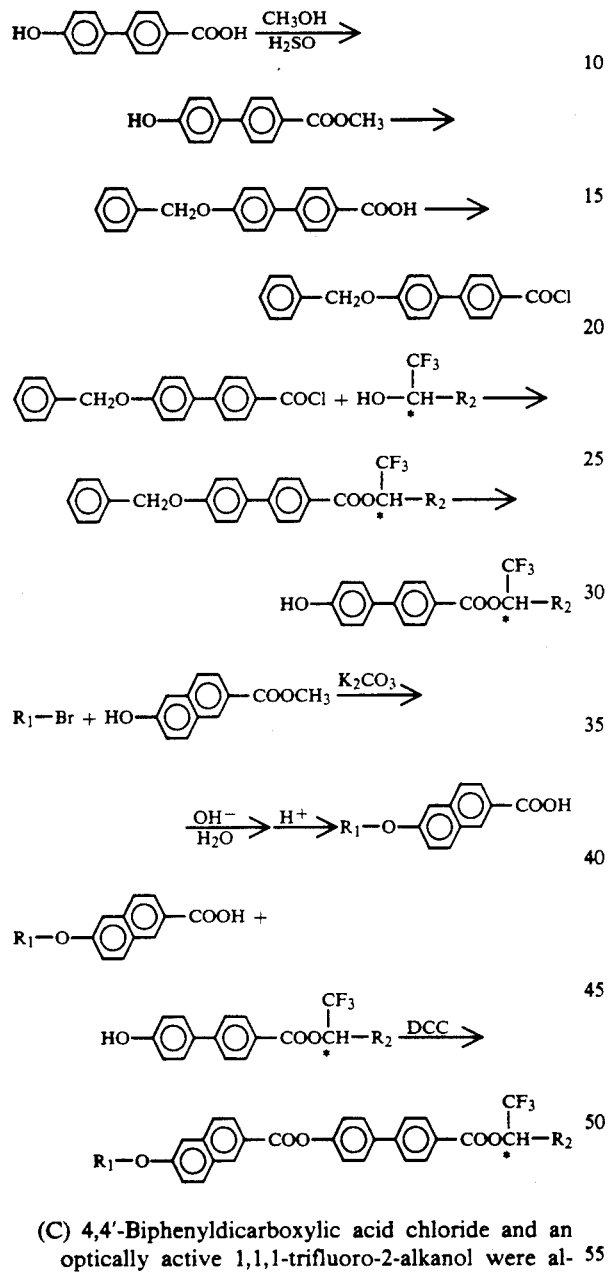

(C) 4,4′-Biphenyldicarboxylic acid chloride and an optically active 1,1,1-trifluoro-2-alkanol were allowed to react to give 4′-(1,1,1-trifluoro-2-alkyloxycarbonyl)biphenyl-4-carboxylic acid chloride.

An alkyl bromide and 2-hydroxy-6-methylcarbonyloxynaphthalene were allowed to react in the presence of potassium carbonate in a solvent such as dimethylformamide and then subjected to hydrolysis with an aqueous sodium hydroxide solution. The hydrolyzed product was allowed to react with the aforementioned 4′-(1,1,1-trifluoro-2-alkyloxycarbonyl) biphenyl-4-carboxylic acid chloride to give 6-alkyloxynaphthalene 4-(1,1,1-trifluoro-2-alkyloxycarbonyl)-biphenyl-4′-carboxylate.

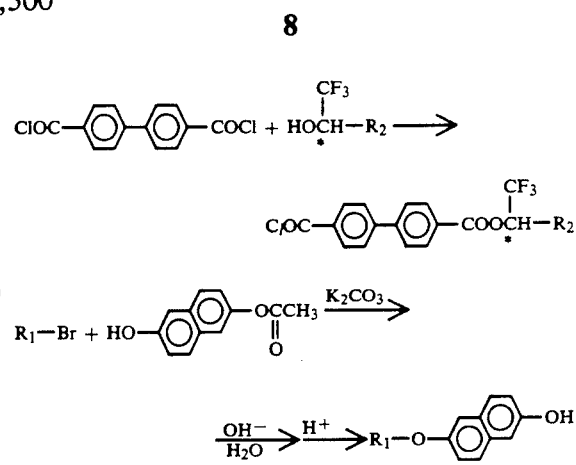

(D) 4-Hydroxybiphenyl-4′-carboxylic acid was dissolved in methanol and heated under refluxing in the presence of concentrated sulfuric acid to give 4-hydroxybiphenyl-4′-carboxylic acid methyl ester. Then the ester and benzyl chloride were dissolved in a solvent such as DMF and allowed to react in the presence of anhydrous potassium carbonate to give 4-benzyloxybiphenyl-4′-carboxylic acid. The carboxylic acid was further allowed to react with thionyl chloride to give 4-benzyloxybiphenyl-4′-carboxylic acid chloride.

An optically active 1,1,1-trifluoro-2-alkanol and the aforementioned acid chloride were allowed to react in a solvent such as methylene chloride to give 1,1,1-trifluoro-2-alkyl 4-benzyloxy-4′-biphenylcarboxylate. The ester was further subjected to hydrogenolysis to give 1,1,1-trifluroro-2-alkyl 4-hydroxybiphenyl-4′-carboxylate.

2,6-Naphthalenedicarboxylic acid chloride and an alkyl alcohol were allowed to react to give 2-alkyloxycarbonylnaphthalene-6-carboxylic acid chloride. The acid chloride was allowed to react with 1,1,1-trifluoro-2-alkyl 4′-hydroxybiphenyl-4-carboxylate to give 2-alkyloxycarbonylnaphthalene-6-carboxylic acid 4-(1,1,1-trifluoro-2-alkyloxycarbonyl)biphenyl ester.

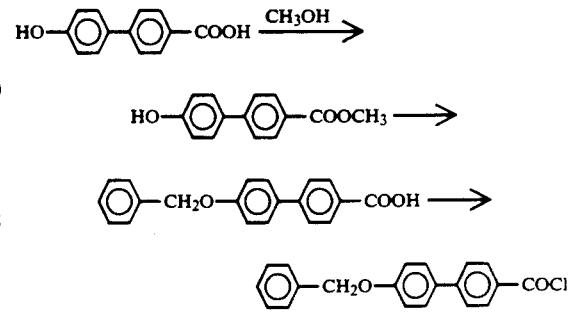

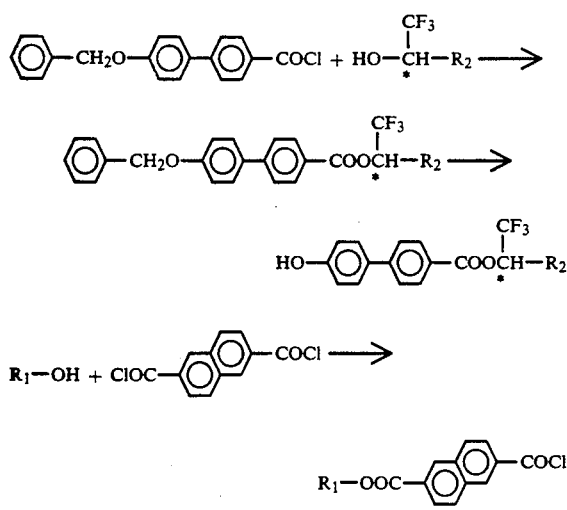

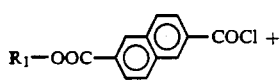

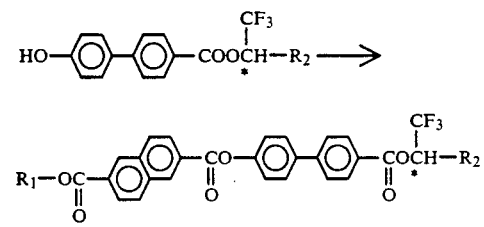

(E) 6-Hydroxy-2-naphthoic acid and acylchloride were allowed to react to give 6-alkylcarbonyloxy-2-naphthoic acid, which was further allowed to react with thionyl chloride to give 6-alkylcarbonyloxy-2-naphthoic acid chloride. The acid chloride was allowed to react with the 1,1,1-trifluoro-2-alkyl 4-hydroxybenzoate obtained in(A) in the presence of dicyclohexylcarbodiimide to give 6-alkylcarbonyloxynaphthalene-2-carboxylic acid 4-(1,1,1-trifluoro-2-alkyloxycarbonyl)phenyl ester.

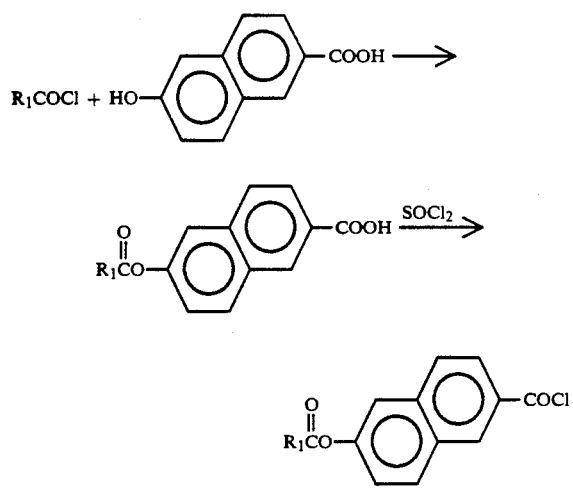

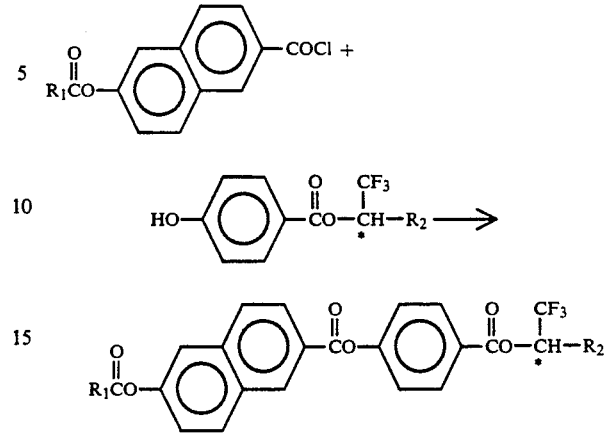

(F) 6-alkylcarbonyloxy-2-naphthoic acid chloride obtained in (E) and 1,1,1-trifluoro-2-alkyl 4'-hydroxybiphenyl-4-carboxylate obtained in (B) were allowed to react to give 6-alkylcarbonyloxynaphthalene-2-carboxylic acid 4'-(1,1,1-trifluoro-2-alkyloxycarbonyl)biphenyl-4ester.

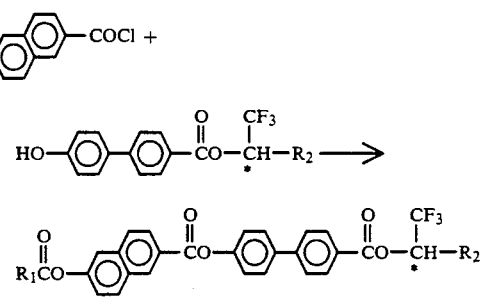

The compounds of the present invention are described with reference to examples without limitation thereto.

EXAMPLE 1

(1) Synthesis of 1,1,1-trifluoro-2-decyl 4-benzyloxybenzoate

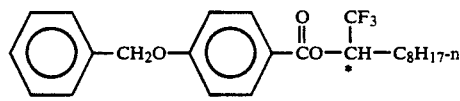

4-Benzyloxybenzoic acid chloride (1.23 g) was dissolved in 10 ml of methylene chloride, and a solution of 1,1,1-trifluoro-2-decanol (0.96 g), dimethylaminopyridine (0.55 g) and triethylamine (0.48 g) in 20 ml of methylene chloride was added portionwise under ice-cooling.

The reaction mixture was warmed to room temperature and allowed to react overnight. The reaction solution was poured into ice-water and extracted with methylene chloride. The methylene chloride phase was washed with dilute hydrochloric acid, water, 1N aqueous sodium hydroxide solution and water in this sequence and dried over anhydrous magnesium sulfate. The solvent was removed to give a crude product, which was subjected to column chromatography on silica gel with toluene and further recrystallized from ethanol to give 1.84 g of the desired product.

(2) Synthesis of 1,1,1-trifluoro-2-decyl 4-hydroxybenzoate

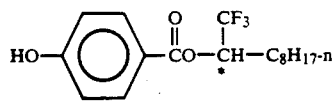

The compound obtained in (1) was dissolved in 15 ml of ethanol and subjected to hydrogenolysis in the presence of 0.36 g of 10 % Pd on carbon under a hydrogen atmosphere to give 1.43 g of the desired compound.

(3) Synthesis of 2-n-decyloxy-6-carboxylnaphthalene

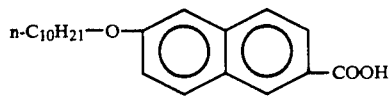

Decyl monobromide (7.0 g), methyl 2-hydroxynaphthalene 6-carboxylate (2.0 g) and anhydrous potassium carbonate (4.0 g) were added to 100 ml of dimethylformamide. After stirring the mixture at 130° C. for 2 hours, it was poured into water. Dilute hydrochloric acid was added to neutralize the solution, which was then extracted with diethyl ether. The residue obtained by removing the solvent was added to a solution comprising 3.3 g of sodium hydroxide, 10 ml of water and 50 ml of ethanol, and the mixture was refluxed for about one day. Dilute hydrochloric acid was added to neutralize the mixture, which was concentrated by removing the solvent. Solid products deposited were collected and recrystallized from a mixed solvent of water-ethanol to give 2.4 g of the desired product.

(4) Synthesis of 2-n-decyloxynaphthalene-6-carboxylic acid 4-(1,1,1-trifluoro-2-decyloxycarbonyl)phenyl ester

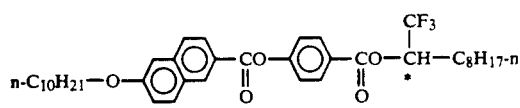

2-n-Decyloxy-6-carboxynaphthalene (0.6 g) obtained in Example 1 - (3) and 1,1,1-trifluoro-2-decyl 4-hydroxybenzoate (0.6 g) obtained in (2) were dissolved in 50 ml of tetrahydrofuran. Dicyclohexylcarbodiimide (0.5 g) and dimethylaminopyridine (0.1 g) were added, and the mixture was stirred at room temperature for a day. After removing the solvent, the residue was dissolved in 50 ml of dichloromethane. The solution was washed with dilute sulfuric acid and water in this sequence, and the organic phase was collected and dried over anhydrous magnesium sulfate. The solvent was removed by distillation, and the residue was purified by column chromatography on silica gel (eluent: hexane/ethyl acetate=20/1) to give 0.55 g of the desired product.

Specific rotation of the product was $[\alpha]_D^{20} = +30.62°$.

The phase transition temperatures (°C.) observed with a microscope equipped with a hot stage was as follows:

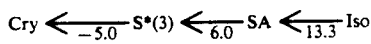

wherein S*(3) represents a liquid crystal phase where the liquid crystal compound shows optically tristable states. The infrared spectrum (KBr) of the desired product is shown in FIG. 5.

EXAMPLE 2

6-(1-octyloxycarbonyl)naphthalene-2-carboxylic acid 4'-(1,1,1-trifluoro-2-octyloxycarbonyl) biphenyl-4-ester

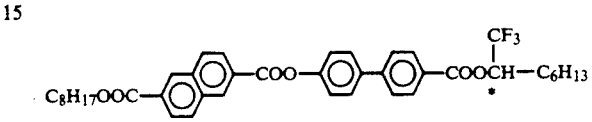

1) 2,6-naphthalene dicarboxylic acid chloride

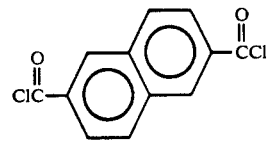

2,6-naphthalene dicarboxylic acid (0.5 g) was added to 15 ml of thionyl chloride, and N,N-dimethylformamide in a very small amount was added to the mixture. The resulting mixture was refluxed for 4 hours. Unaltered thionyl chloride was removed by evaporation to give 0.45 g of the desired compound.

Synthesis of 4'-(1,1,1-trifluoro-2-octyloxycarbonyl)-benzyloxybiphenyl

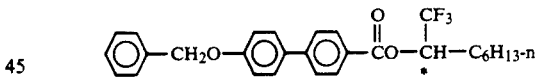

4'-benzyloxybiphenyl-4-carboxylic acid chloride (4.3 g) was dissolved in 50 ml of methylene chloride, and a solution of 1,1,1-trifluoro-2-octanol (2.0 g), dimethylaminopyridine (0.6 g) and triethylamine (1.7 g) in 50 ml of methylene chloride was added to the carboxylic acid chloride solution in small portions under ice-cooling.

The reaction mixture was warmed to a room temperature and allowed to react a whole day and night. The reaction solution was poured into ice-water and extracted with methylene chloride, and the methylene chloride phase was washed with dilute hydrochloric acid, water, 1N aqueous sodium carbonate solution and water in this sequence and dried over anhydrous magnesium sulfate. The solvent was removed by evaporation to give a crude product, which was treated with a toluene-silica gel column chromatograph and further recrystallized from ethanol to give 3.0 g of the desired product.

3) Synthesis of 4-(1,1,1-trifluoro-2-octyloxycarbonyl)-4'-hydroxybiphenyl

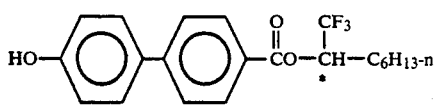

The compound obtained in 1) was dissolved in 100 ml of methanol and subjected to hydrogenolysis under a hydrogen atmosphere in the presence of 10% Pd on carbon to give 2.2 g of the desired product.

4) 6-(1-octyloxycarbonyl)naphthalene-2-carboxylic acid 4'-(1,1,1-trifluoro-2-octyloxycarbonyl)biphenyl4-ester

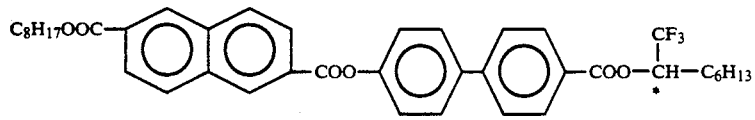

Into a solution of 4-(1,1,1-trifluoro-2-octyloxycarbonyl)-4'-hydroxybiphenyl (0.4 g) obtained in 3) above 1-octanol (0.14 g) and triethylamine (0.22 g) in 30 ml of methylene chloride was added dropwise a solution of 2,6-naphthalene dicarboxylic acid chloride (0.3 g) obtained in 1) in 30 ml of methylene chloride Then, dimethylaminopyridine (0.1 g) was added, and the resulting mixture was stirred for about 20 hours.

The reaction mixture was then poured into ice-water and extracted with methylene chloride. The methylene chloride layer was washed with dilute hydrochloric acid, water, 1N aqueous sodium hydrogen carbonate solution and water in this sequence and dried over anhydrous magnesium sulfate. The solvent was removed by evaporation to give a crude product, which was treated by silica gel column chromatography (development solvent: hexane/ethyl acetate=10/0.5) to give 0.1 g of the desired product.

Phase transition temperatures (°C.) observed under a polarizing microscope using a hot stage were as follows:

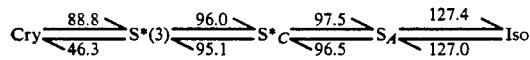

wherein S*(3) shows the optically tristable liquid crystal phase.

Figure 6:
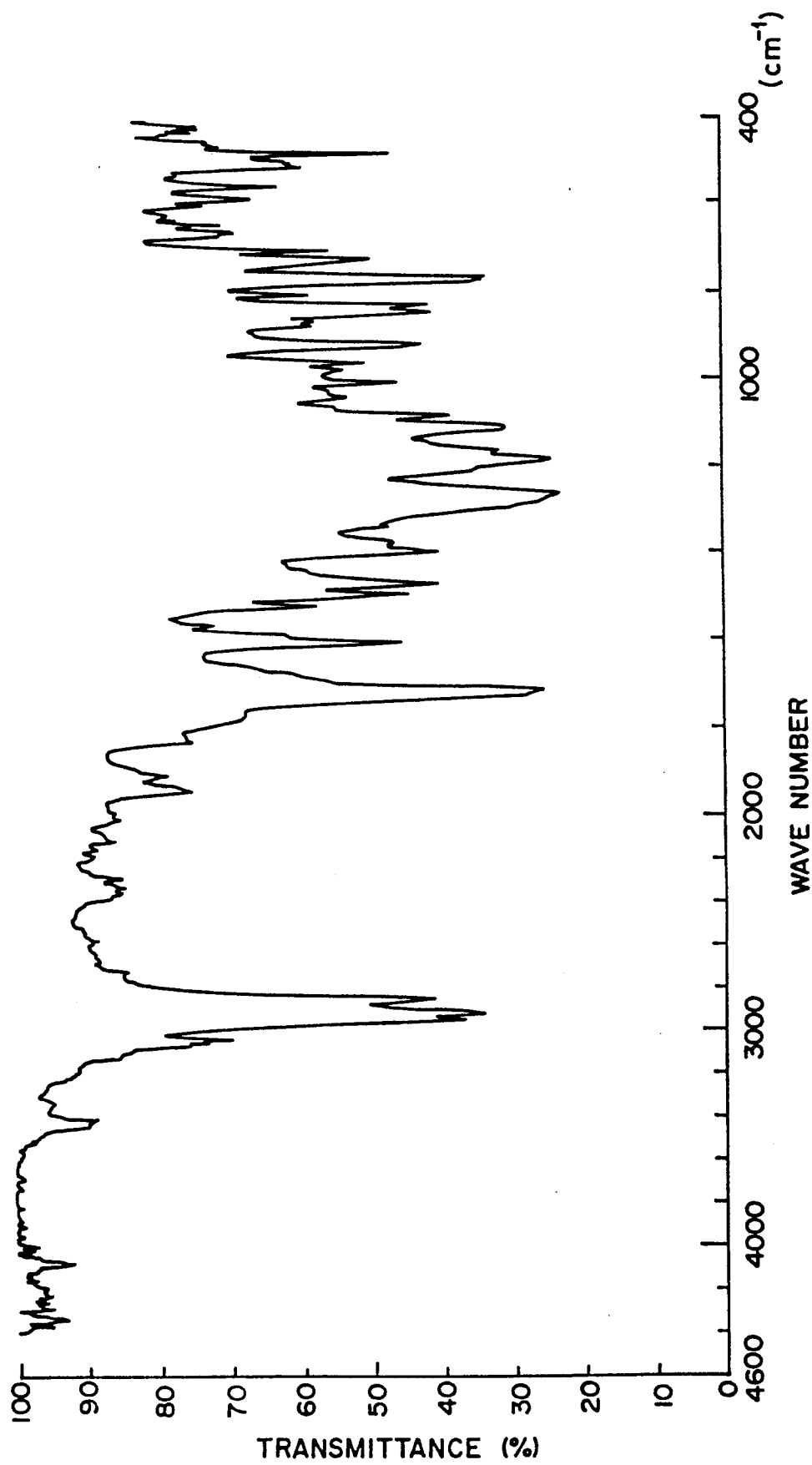

The infrared spectrum (KBr) of the desired product is shown in FIG. 6.

EXAMPLE 3

(1) Synthesis of 4'-(1,1,1-trifluoro-2-octyloxycarbonyl)biphenyl-4-carboxylic acid chloride

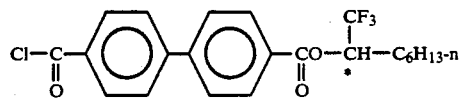

An optically active 1,1,1-trifluoro-2-octanol (1.8 g) and triethylamine (1.1 g) were dissolved in 80 ml of methylene chloride. To this solution was added slowly 4,4'-biphenyldicarboxylic acid chloride (2.3 g). Dimethylaminopyridine (0.3 g) was further added, and the mixture was stirred for a day. The solvent was removed by distillation to give 4.0 g of residue containing 4-(1,1,1-trifluoro-2-octyloxycarbonyl)biphenyl-4'-carboxylic acid chloride.

(2) Synthesis of 2-n-decyloxy-6-hydroxynaphthalene

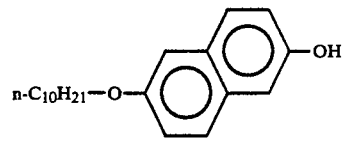

Decyl monobromide (7.0 g), 2,6-dihydroxynaphthalene (5.0 g) and anhydrous potassium carbonate (4.0 g) 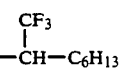 were added to 100 ml of dimethylformamide. After stirring at 130° C. for 2 hours, the reaction solution was poured into water. Dilute hydrochloric acid was added to neutralize the solution, which was extracted with diethyl ether. The extract was distilled to remove the solvent to obtain the titled compound as residue (8.0 g).

(3) Synthesis of 6-n-decyloxynaphthalene 4'-(1,1,1-trifluoro-2-octyloxycarbonyl)biphenyl-4carboxylate

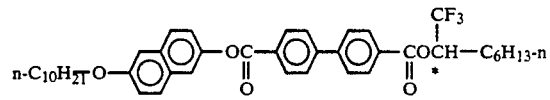

2-n-Decyloxy-6-hydroxynaphthalene (0.5 g) obtained in (2) of Example 3 and triethylamine (0.25 g) were dissolved in 50 ml of methylene chloride The residue (about 4.0 g) containing 4'-(1,1,1-trifluoro-2-octyloxycarbonyl)biphenyl-4-carboxylic acid chloride obtained in (1) of Example 3 was added gradually to the solution above. Dimethylaminopyridine (0.02 g) was further added, and the mixture was stirred for a day. The solution was washed with dilute sulfuric acid and water in this sequence, and the organic layer was collected and dried over anhydrous magnesium sulfate. The solvent was removed by distillation, and the residue was purified by column chromatography on silica gel (eluent: hexane/ethyl acetate=20/1) to obtain 0.46 g of the desired product.

The product had a specific rotation of $[\alpha]_D^{20} = +37.67°$ and the following phase transition temperatures (°C.) were observed under a microscope equipped with a hot stage:

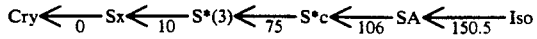

Figure 7:
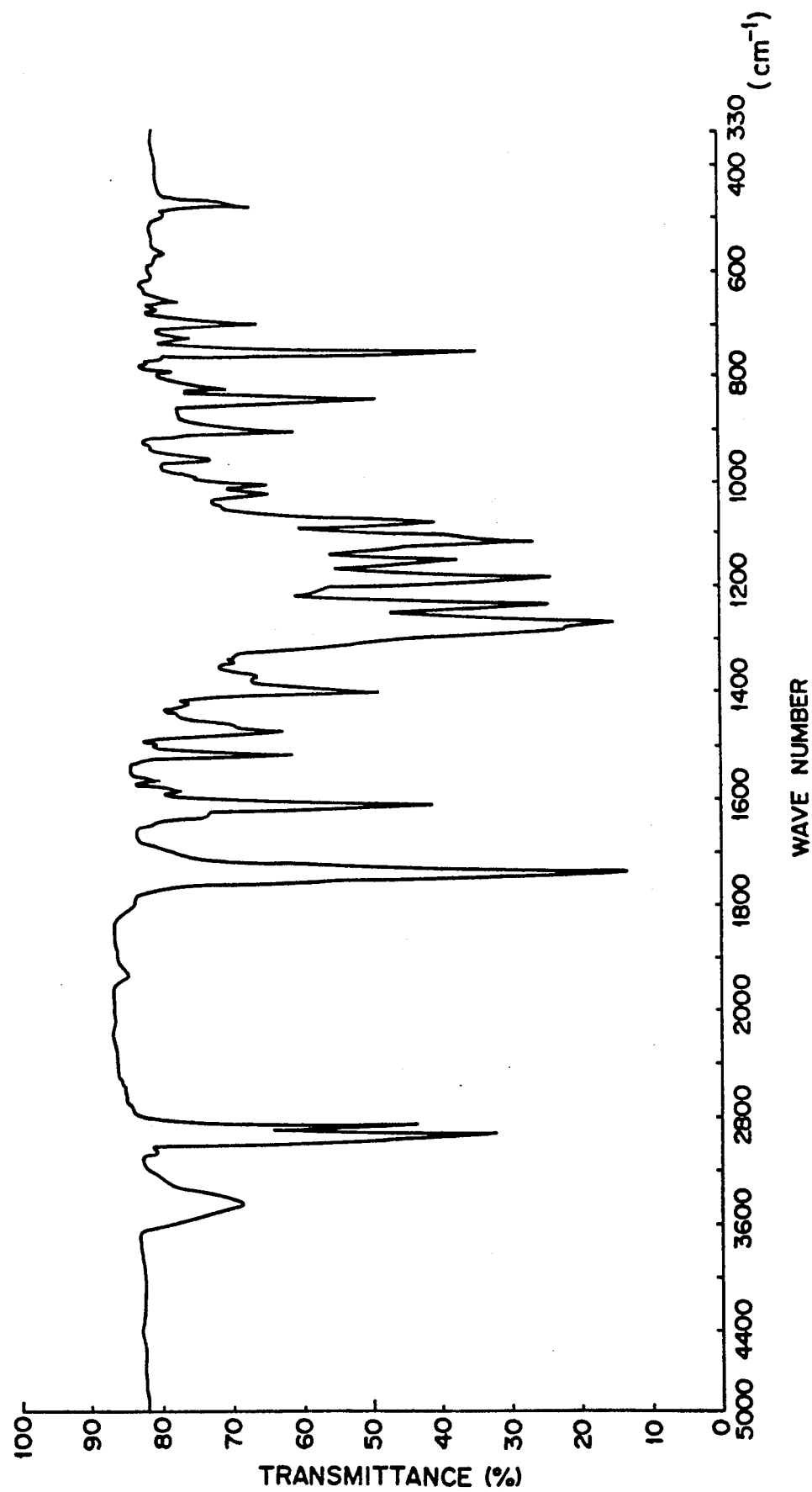

Sx is a phase of a higher order having a response to electric field. The infrared spectrum (KBr) of the desired product is shown in FIG. 7.

EXAMPLE 4

(1) Synthesis of 6-n-decyloxynaphthalene-2-carboxylic acid 4-(1,1,1-trifluoro-2-octyloxycarbonyl)biphenyl-4'-ester

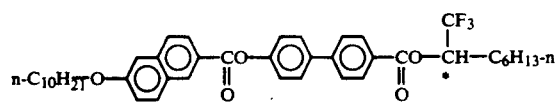

2-n-Decyloxy-5-carboxynaphthalene (0.6 g) obtained in (3) of Example 1 and optically active 1,1,1-trifluoro-2-octyl 4'-hydroxybiphenyl-4-carboxylate (0.65 g) obtained in (1) of Example 2 were dissolved in 50 ml of tetrahydrofuran. Dicyclohexylcarbodiimide (0.6 g) and dimethylaminopyridine (0.1 g) were added to the solution above, and the mixture was stirred at room temperature for a day. After removing the solvent by distillation, the residue was dissolved in 50 ml of dichloromethane. The solution was washed with dilute sulfuric acid and water in this sequence, and the organic layer was collected and dried over anhydrous magnesium sulfate. The solvent was removed by distillation, and the residue was purified by chromatography on silica gel (eluent: hexane/ethyl acetate=20/1) to give 0.6 g of the desired product.

The product had a specific rotation of $[\alpha]_D^{20} = +35.52°$ and the following phase transition temperatures (°C.) were observed under a microscope equipped with a hot stage:

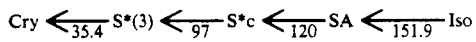

Figure 8:
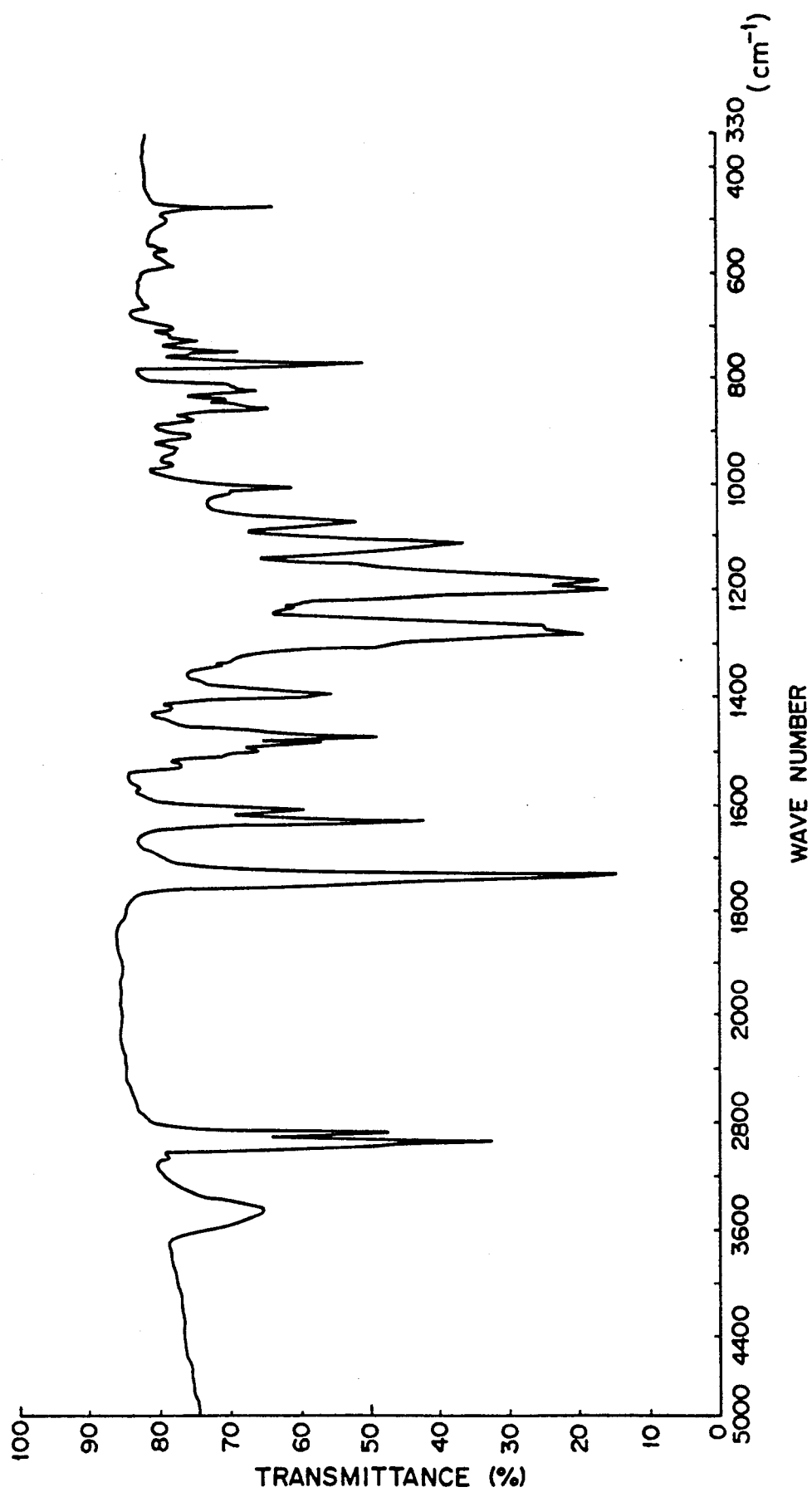

The infrared spectrum (KBr) of the desired product is shown in FIG. 8.

All of the novel liquid crystals of the present invention exhibit tristable states when in S*(3) phase and have a wide range of applications such as a display device or a switching device using the tristable states.

EXAMPLE 5

6-nonanoyloxy-2-naphthoic acid 4'-(1,1,1-trifluoro-2-octyloxycarbonyl)biphenyl-4-ester

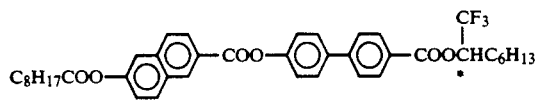

1) Synthesis of 4'-(1,1,1-trifluoro-2-octyloxycarbonyl)-4-benzyloxybiphenyl

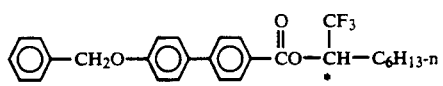

4'-benzyloxybiphenyl-4-carboxylic acid chloride (4.3 g) was dissolved in 50 ml of methylene chloride, and a solution of optically active 1,1,1-trifluoro-2-octanol (2.0 g), dimethylaminopyridine (0.6 g) and triethylamine (1.7 g) in 50 ml of methylene chloride was added to the carboxylic acid chloride solution in small portions under ice-cooling.

The reaction mixture was warmed to a room temperature and allowed to react a whole day and night. The reaction solution was poured into ice-water and extracted with methylene chloride, and the methylene chloride phase was washed with dilute hydrochloric acid, water, 1N aqueous sodium carbonate solution and water in this sequence and dried over anhydrous magnesium sulfate. The solvent was removed by evaporation to give a crude product, which was treated with a toluene-silica gel column chromatograph and further recrystallized from ethanol to give 3.0 g of the desired product 2) Synthesis of 4-(1,1,1-trifluoro-2-octyloxycarbonyl)-4'-hydroxybiphenyl

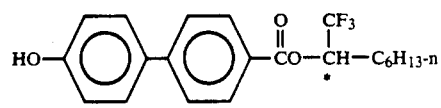

The compound obtained in 1) was dissolved in 100 ml of methanol and subjected to hydrogenolysis under a hydrogen atmosphere in the presence of 10% Pd on carbon to give 2.2 g of the desired product.

3) Synthesis of 6-n-nonanoyloxy-2-naphthoic acid

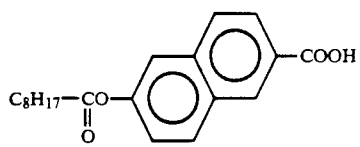

6-hydroxy-2-naphthoic acid (3.0 g) and triethylamine (2.4 g) were dissolved in 30 ml of dichloromethane. Nonanoyl chloride (4.0 g) and dimethylaminopyridine (0.2 g) were added to the solution, and the mixture was stirred at room temperature for about 20 hours. Dilute hydrochloric acid was added, and the organic layer was separated in a separating funnel. The solvent was removed by evaporation, and the residue was dried after washing with n-hexane to give 4.5 g of the desired product.

4) Synthesis of 6-n-nonanoyloxy-2-naphthoic acid chloride

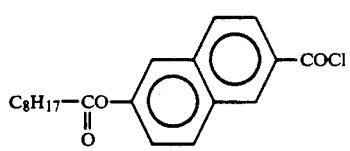

4-n-nonanoyloxy-2-naphthoic acid (4.5 g) was added to thionyl chloride (10.0 g), and N,N-dimethylformamide in a very small amount was added to the mixture. The resulting mixture was refluxed for 4 hours. Unaltered thionyl chloride was removed by evaporation to give 4.5 g of the desired compound.

Synthesis of 6-nonanoyloxy-2-naphthoic acid 4'-(1,1,1-trifluoro-2-octyloxycarbonyl)biphenyl-4-ester

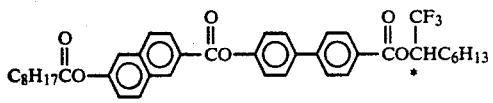

4-(1,1,1-trifluoro-2-octyloxycarbonyl)-4'-hydroxybiphenyl (0.5 g) synthesized in 2) and triethylamine (0.16 g) were dissolved in 30 ml of methylene chloride. 6-n-nonanoyloxy-2-naphthoic acid chloride (0.7 g) synthesized in 4) was dissolved in 30 ml of methylene chloride and added dropwise to the aforementioned solution. Dimethylaminopyridine (0.05 g) was further added, and the mixture was stirred at room temperature for a whole day and night. The reaction mixture was poured into water, and the solution was adjusted neutral to separate the methylene chloride layer. After the organic layer was dried over anhydrous magnesium sulfate, methylene chloride was removed by evaporation. The residue was purified by silica gel column chromatography (eluent: hexane/ethyl acetate=20/1) to give 0.1 g of the desired compound.

Figure 9:
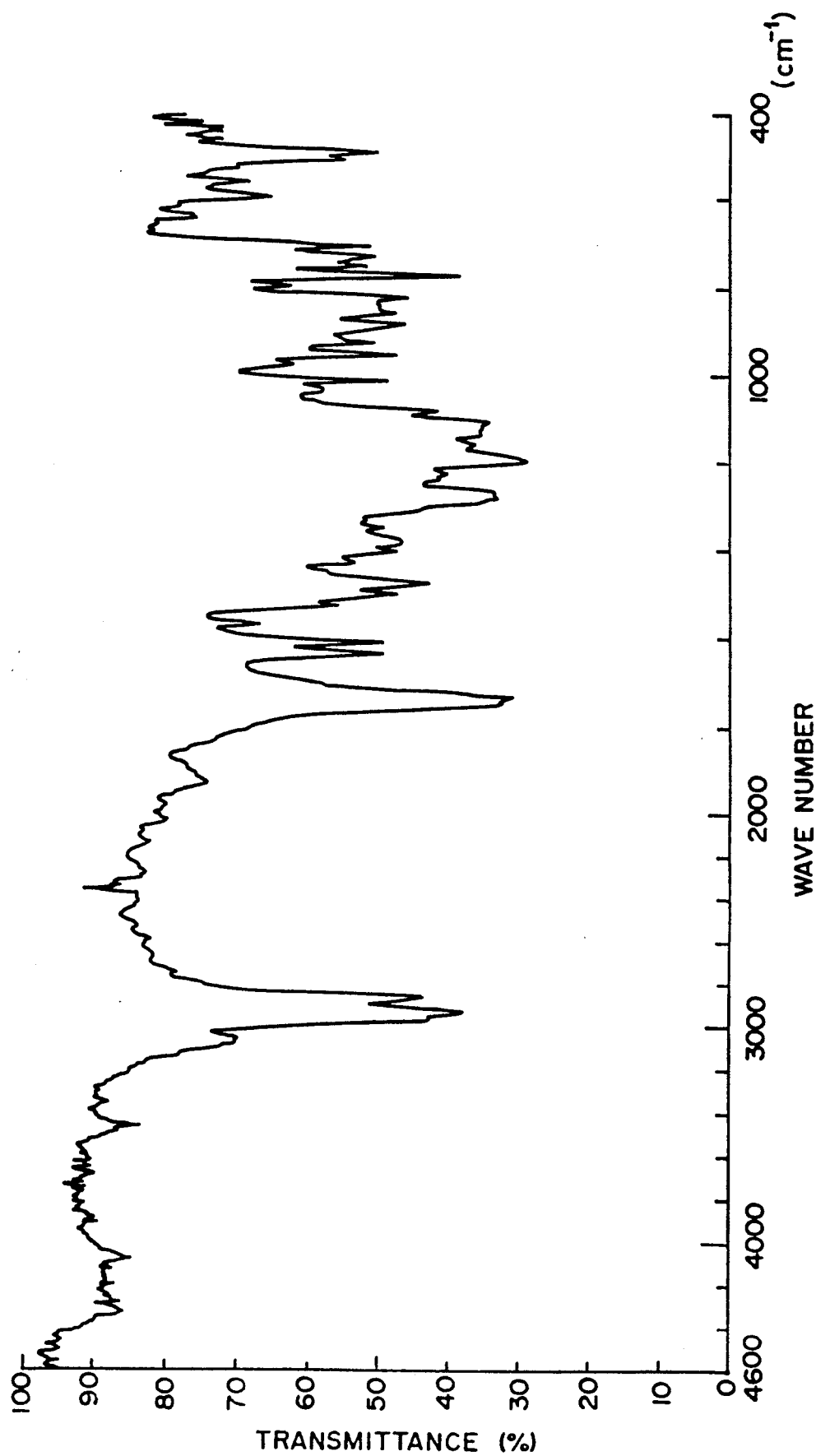

The phase transition temperatures (°C.) observed with a microscope equipped with a hot stage were as follows:

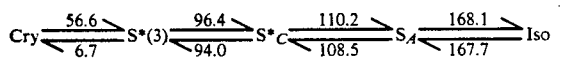

wherein S*(3) means a liquid crystal phase where the liquid crystal shows optically tristable states. The infrared spectrum (KBr) of the desired product is shown in FIG. 9.

Figure 14A:
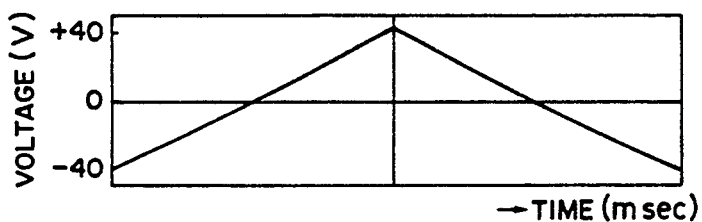
FIGS. 14A-14E show the triangular wave voltage applied to liquid crystal cells and the hysteresis curves when the triangular wave voltage was applied to the liquid crystal cells.
Figure 14B:
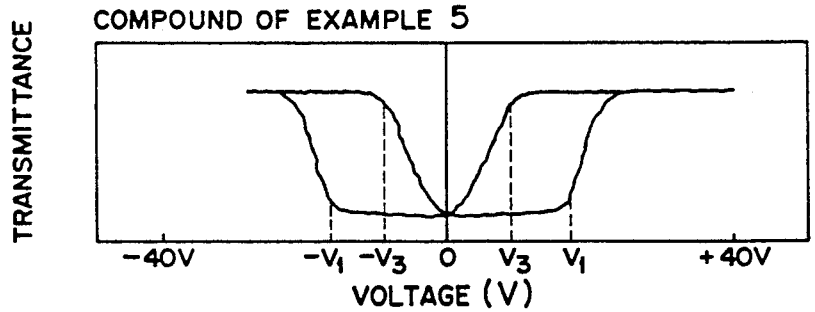

The compound in Example 5 exhibits the most distinctive hysteresis as will be mentioned in Example 10 or FIG. 14(B) and possesses a large memory margin and a quick response time as will be mentioned in Examples 11 and 12.

EXAMPLE 6

6-nonanoyloxy-2-naphthoic acid 4'-(1,1,1-trifluoro-2-octyloxycarbonyl)phenyl-4-ester

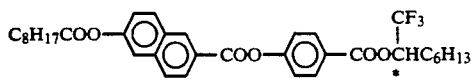

The desired product was obtained by repeating 1) in Example 5 except using 4-benzyloxybenzoic acid chloride in place of 4'-benzyloxybiphenyl-4-carboxylic acid chloride.

The phase transition temperatures (°C.) observed with a microscope equipped with a hot stage were as follows:

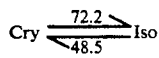

Figure 10:
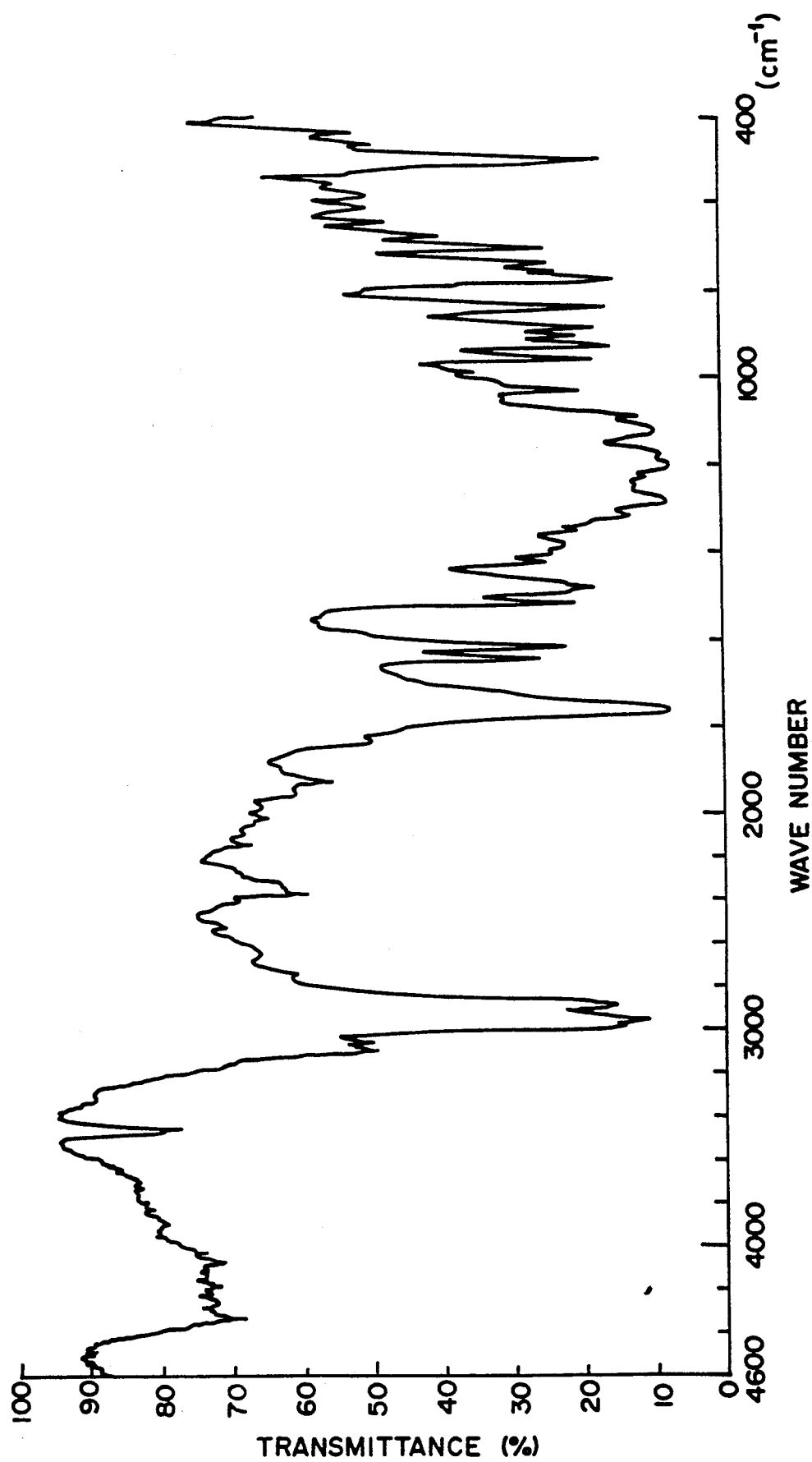

The infrared spectrum (KBr) of the desired product is shown in FIG. 10.

EXAMPLE 7

4'-(1,1,1-trifluoro-2-octyloxycarbonyl)-biphenyl-4-carboxylic acid 6-nonanoyloxynaphthalene-2-ester

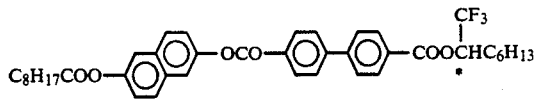

1) 2-hydroxy-6-nonanoyloxynaphthalene

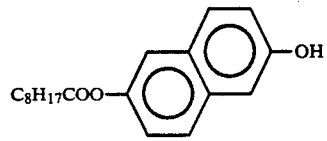

2,6-dihydroxynaphthalene (0.48 g) and triethylamine (0.31 g) were dissolved in 20 ml of dichloromethane. Nonanoyl chloride (0.55 g) and dimethylaminopyridine (0.13 g) were added to the solution, and the mixture was stirred at room temperature for about 20 hours. The reaction mixture was poured into ice-water, extracted with dichloromethane and dried over anhydrous magnesium sulfate, and the solvent was removed by evaporation to give a crude product, which was treated with a silica gel column chromatograph (eluent: hexane/ethyl acetate=10/2) to give 0.29 g of the desired product.

2) 4,4'-biphenyldicarboxylic acid dichloride

4,4'-biphenyldicarboxylic acid (3.3 g) was added to 20 ml of thionyl chloride, and N,N-dimethylformamide in a very small amount was added to the mixture. The resulting mixture was refluxed for 4 hours. Unaltered thionyl chloride was removed by evaporation to give 3.8 g of the desired compound.

3) 4'-(1,1,1-trifluoro-2-octyloxycarbonyl)biphenyl4-carboxylic acid 6-nonanoyloxynaphthalene-2-ester

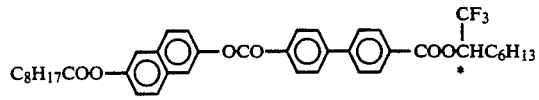

A solution of 4,4'-biphenyldicarboxylic acid dichloride (0.42 g) obtained in 2) in 20 ml of methylene chloride was added in small portions to a solution of optically active 1,1,1-trifluoro-2-octanol (0.22 g), dimethylaminopyridine (0.1 g) and triethylamine (0.25 g) in 20 ml of methylene chloride under ice-cooling. After the mixture was stirred for about 20 hours, a solution of 2-hydroxy-6-nonanoyloxynaphthalene (0.29 g) obtained in 1) in 20 ml of methylene chloride was added in small portions, and the mixture was stirred for about 20 hours. The reaction mixture was then poured into ice-water and extracted with methylene chloride. The methylene chloride layer was washed with dilute hydrochloric acid, water, 1N aqueous sodium carbonate solution and water in this sequence and dried over anhydrous magnesium sulfate. The solvent was removed by evaporation to give a crude product, which was treated by silica gen column chromatography (eluent: hexane/ethyl acetate = 10/1.5) to give 0.11 g of the desired product.

Phase transition temperatures (°C.) observed under a polarizing microscope equipped with a hot stage were as follows:

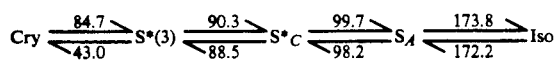

wherein S*(3) means the optically tristable liquid crystal phase.

Figure 11:
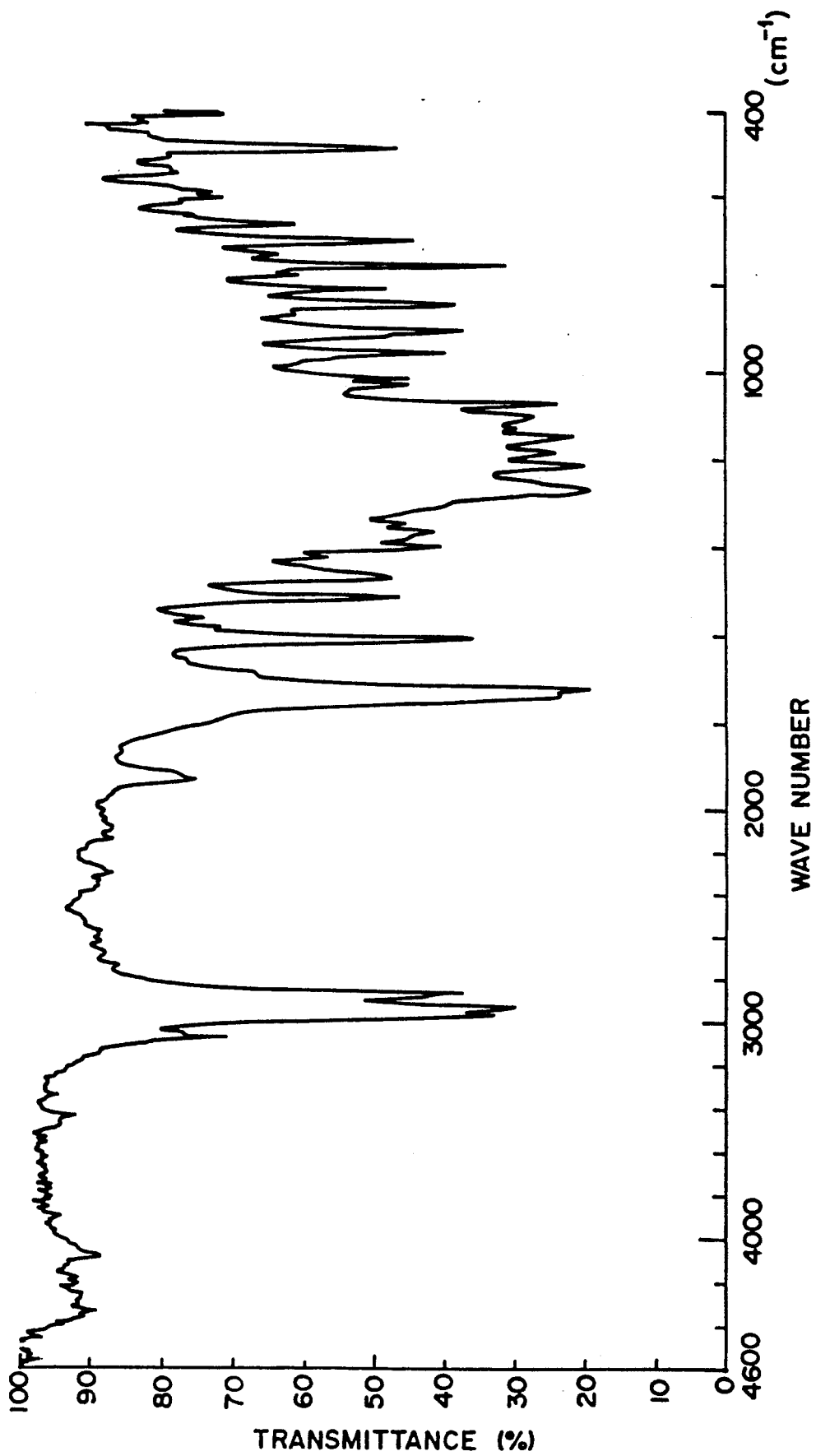

The infrared spectrum (KBr) of the desired product is shown in FIG. 11.

EXAMPLE 8

6-octyloxycarbonylnaphthalene-2carboxylic acid 4-(1,1,1-trifluoro-2-octyloxycarbonyl) phenyl ester

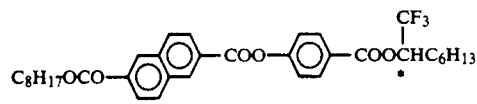

4-(1,1,1-trifluoro-2-octyloxycarbonyl) hydroxyphenyl was obtained by repeating 1) and 2) in Example 5 except that 4-benzyloxybenzoic acid chloride was used in place of 4'-benzyloxy biphenyl-4-carboxylic acid chloride The desired product was obtained by following 4) in Example 2 with 4 (1,1,1 trifluoro-2-octyloxycarbonyl)hydroxyphenyl in place of 4-(1,1,1-trifluoro-2-octyloxycarbonyl) 4'-hydroxybiphenyl.

Phase transition temperatures (°C.) observed under a polarizing microscope equipped with a hot stage were as follows:

EXAMPLE 9

4'-(1,1,1-trifluoro-2-octyloxycarbonyl) biphenyl-4-carboxylic acid 6-(octyloxycarbonyl)naphthalene-2-ester

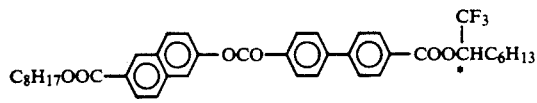

1) 2-hydroxy-6-octyloxycarbonylnaphthalene

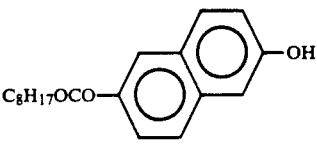

2-benzyloxynaphthalene-6-carboxylic acid chloride (6.4 g) was dissolved in 50 ml of methylene chloride and added in small portions to a solution of 1-octanol (2.6 g), dimethylaminopyridine (0.7 g) and triethylamine (2.1 g) in 30 ml of methylene chloride under ice-cooling. After the reaction mixture was stirred for about 20 hours, it was poured into ice-water and extracted with methylene chloride. The solvent was removed by evaporation to give a crude product, which was then subjected to silica gel column chromatography (eluent: hexane/ethylacetate = 10/0.5) to give 2.6 g of 2-benzyloxy-6-octyloxycarbonylnaphthalene.

The compound was next dissolved in 30 ml of ethanol. After stirring for about 20 hours in the presence of 0.15 g of Pd on carbon under hydrogen atmosphere, the catalyst was removed by filtration, and ethanol was removed by evaporation to give 1.1 g of the desired product.

2) 4'-(1,1,1-trifluroro-2-octyloxycarbonyl(biphenyl-4-carboxylic acid 6-(octyloxycarbonyl)naphthalene-2-ester

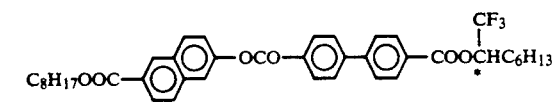

Optically active 1,1,1-trifluoro-2-octanol (0.5 g), dimethylformamide (0.35 g) and triethylamine (0.64 g) were dissolved in 20 ml of methylene chloride. To this solution was added in small portions a solution of 4,4'-biphenyldicarboxylic acid dichloride (1.6 g) obtained in 2) of Example 7 in 50 ml of methylene chloride under ice-cooling, and the mixture was stirred for about 20 hours. Next, 2-hydroxy-6-octyloxycarbonylnaphthalene (0.86 g) obtained in 1) was dissolved in 30 ml of methylene chloride and added in small portions to the reaction mixture. The resulting mixture was stirred for about 20 hours.

The reaction mixture was poured into ice-water and extracted with methylene chloride. The methylene chloride layer was washed with dilute hydrochloric acid, water, 1N aqueous sodium hydrogen carbonate solution and water in this sequence and dried over anhydrous magnesium sulfate. The solvent was removed by evaporation to give a crude product, which is subjected to silica gel column chromatography (eluent: hexane/ethyl acetate = 10/0.5) to give 0.3 g of the desired product.

Figure 12:
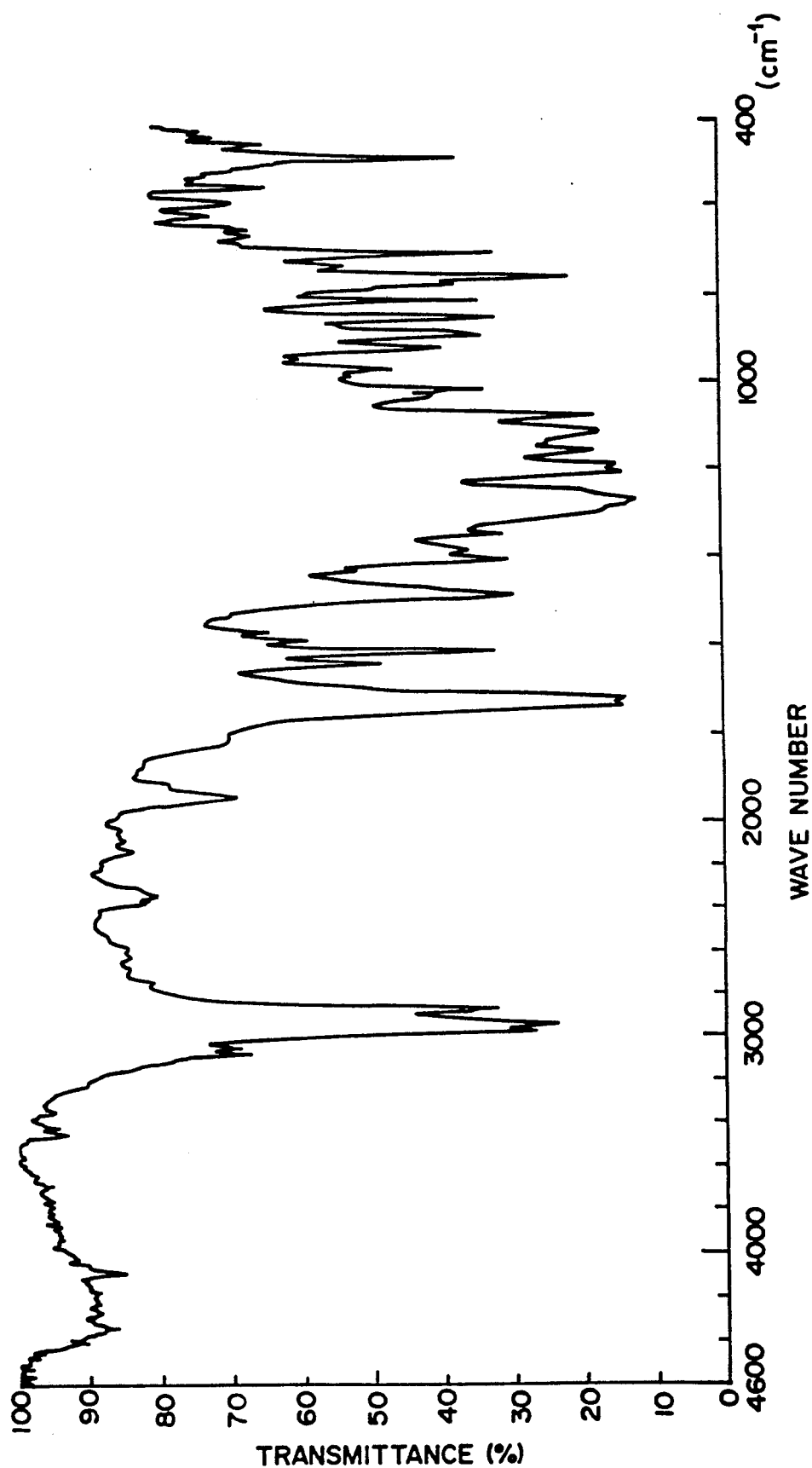

Phase transition temperatures (°C.) observed under a polarizing microscope equipped with a hot stage were as follows:

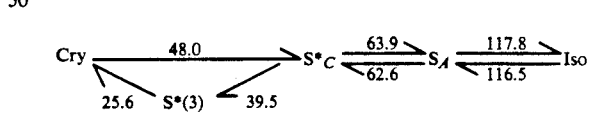

wherein S* (3) means the tristable state liquid crystal phase. The infrared spectrum (KBr) of the desired product is shown in FIG. 12.

EXAMPLE 10

Hysteresis curves of the compounds obtained in Examples 2, 5, 7 and 9 were measured with the following apparatuses:

A polarizing optical microscope (OLYMPUS model BHSP)
A photometer (SANKEI SPS-5A)
A photo cell (Hamamatsu R-636)
A high speed power amplifier (NF 4005)

A digitizing osilloscope (YHP HP 54501A)
A function generator (YHP HP 3314A)
A hot Stage (Metler FP 82)
A central processor (Metler FP 80)

SAMPLE PREPARATION

Sample cells were constructed from two glass substrates with patterned ITO (indium-tin-oxide). The substrates were initially spin-coated with polyimides (LX500 produced by Hitachi Kasei Ltd.) and were then rubbed with nylon cloths on a rotating cylinder under several kinds of rubbing conditions. The sample cells were composed of two substrates thus processed, the rubbing directions of which were mutually parallel The cell spacing was 1.6 μm. After the cell was filled with antiferroelectric liquid crystal by capillary suction in the isotropic phase, it was cooled slowly (−0.1-, −1° C./min) to the S* (3) phase.

EVALUATION OF SAMPLES

Figure 13:
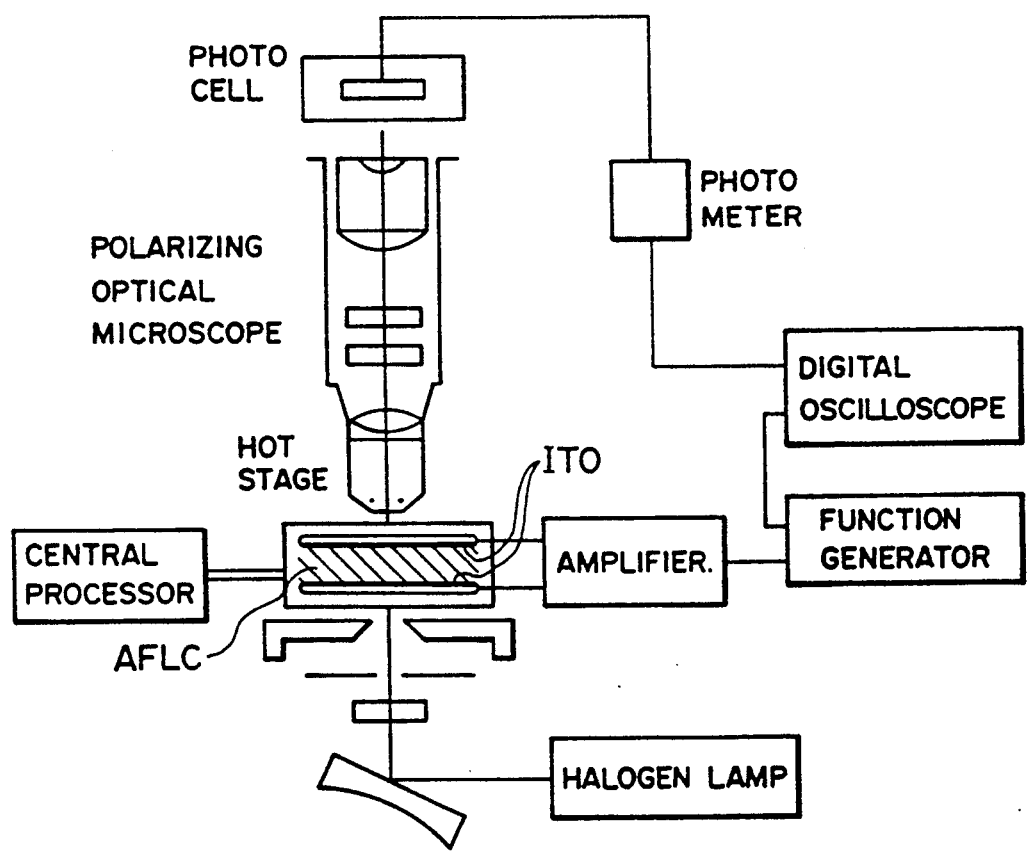
FIG. 13 shows an apparatus for measuring a hysteresis in Example 10.

The orientation of the sample was observed under a polarizing microscope. In order to control the sample temperature, a hot stage (Mettler IP82) and a central processor (Mettler FP80) were used. The electrooptical properties were evaluated by the measurement system, as shown in FIG. 13. The light transmitted through the sample cell was detected by a photo cell. Pulses were synthesized in a function generator and were supplied to the sample cells through a bipolar amplifier.

A liquid crystal cell having a rubbed polyimide oriented film on the ITO electrode substrate plate and a thickness of 1.6 μm was filled with the liquid crystal compound obtained in Example 5, i.e., 6-nonanoyloxy-2-naphthoic acid 4′-(1,1,1-trifluoro-2-octyloxycarbonyl)biphenyl-4-ester, in an isotropic phase to make a liquid crystal film cell.

The liquid crystal cell thus prepared was arranged on a polarizing microscope equipped with a photomultiplier which was made of two polarizing plates orthogonalized to each other so that darkness is realized at a voltage of 0 V.

The liquid crystal cell was slowly cooled down to the SA phase at a temperature gradient in the range of 0.1–1.0° C./min. The liquid crystal cell was further cooled down, and a triangular wave voltage of ±40 V and 1 Hz was applied (FIG. 14A). From the relationship between the applied voltage and the transmittance, a hysteresis curve shown in FIG. 14B was obtained. In the switching process from 0 to $+V_1$, the liquid crystal cell maintains the dark state. The transmittance steeply increases at the voltage of $+V_1$ and the cell displays the light state. In the switching process from +40 to $+V_3$, the liquid crystal cell maintains the light state and steeply starts changing into the dark state at the voltage of $+V_3$. In the switching process from 0 to $-V_1$, it again maintains the dark state and changes into the light state after the steep increase of the transmittance at $-V_1$. In the switching process from −40 V to $-V_3$, the liquid crystal cell again maintains the light state and steeply starts changing into the dark state at the voltage of $-V_3$. It was observed that the liquid crystal cell follows the three states of light, dark and light with switching when the applied voltage varies within the range of +40 V to −40 V. It was thus confirmed that the liquid crystal cell possesses three stable orientation states.

Figure 14C:
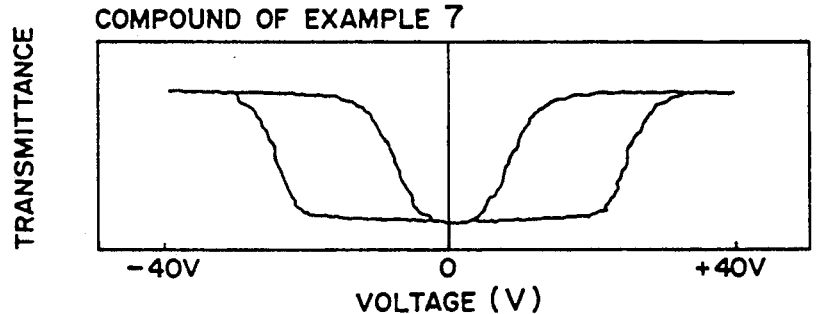
Figure 14D:
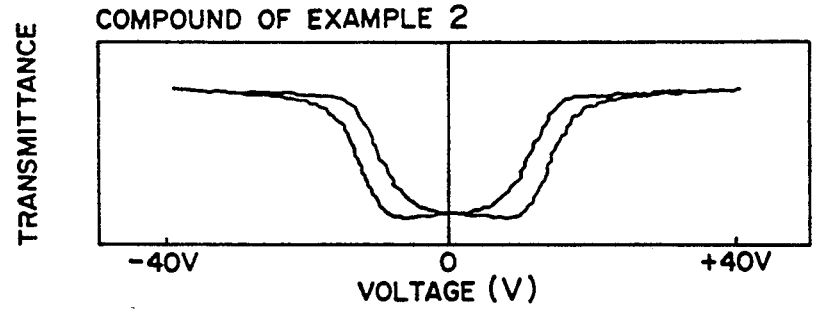
Figure 14E:
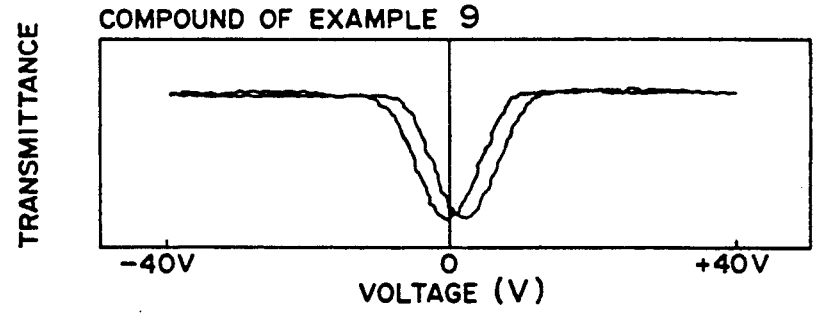

As for the liquid crystal compounds obtained in Examples 2, 7 and 9, hysteresis curves shown in FIGS. 14C–14E were obtained by the same manner as above.

The compounds obtained in Example 5 and 7 exhibited distinctive hysteresis.

EXAMPLE 11

Memory margen was measured for the compounds obtained in Examples 2, 5, 7 and 9. Memory margin was calculated from each hysteresis curve.

Figure 15:
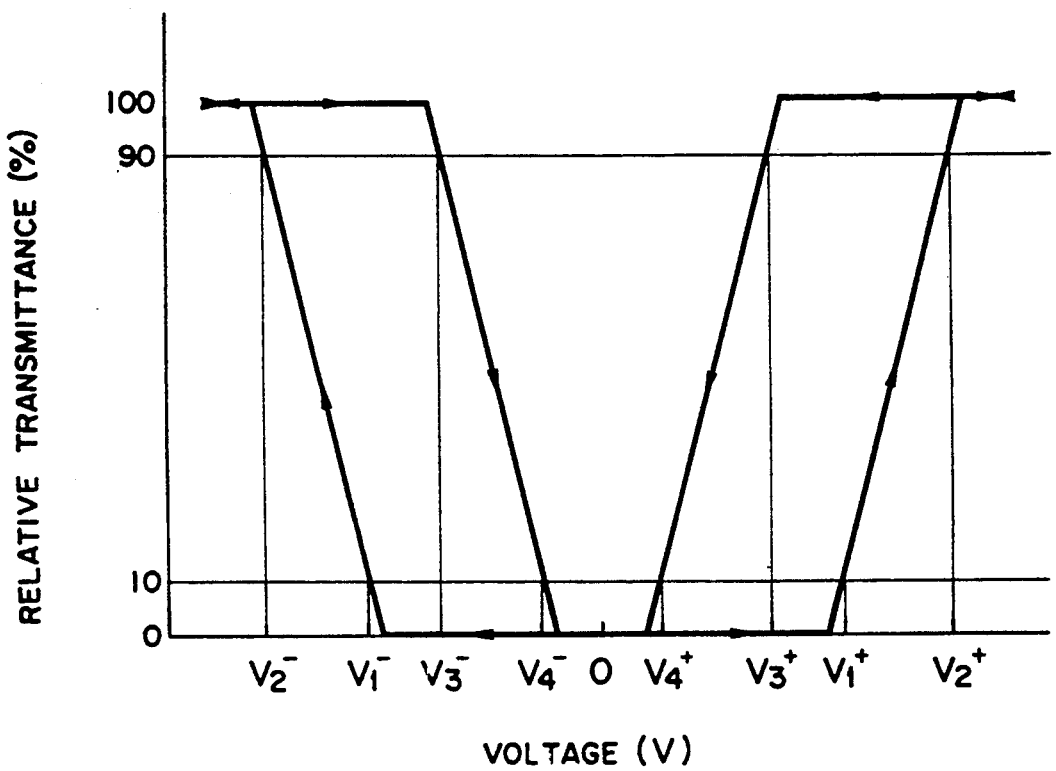
FIG. 15 shows the illustration for calculating the memory margin.

Hysteresis curves were obtained by the method described in Example 10. In FIG. 15, the relative transmittance is represented by 0% at the voltage of 0 V and 100% at the voltage where the maximum transmittance is obtained. The voltage corresponding to the transmittance 10% is represented by $V_1^+$, and the voltage needed for the transmittance of 90% is represented by $V_2^+$. When the transmittance varies from 100% to 90%, the corresponding voltage is represented by $V_3^+$. When the transmittance reaches 10%, the voltage is represented by $V_4^+$, $V_1^-$, $V_2^-$, $V_3^-$ and $V_4^-$ are defined similarly. Memory margin M is calculated from the following equation:

$$M = \frac{V_1^+ - V_3^+}{V_2^+ - V_1^+} = \frac{V_1^- - V_3^-}{V_2^- - V_1^-}$$

The results are shown in Table 1.

TABLE 1

| Compound of Example | Memory Margin (M) | T − TcA (°C.) |
|---|---|---|
| 5 | 1.58 | −20 |
| 7 | 0.81 | −20 |
| 2 | none | −20 |
| 9 | none | −10 |

Only the compound obtained in Example 5 showed a memory margin of 1 or more.

EXAMPLE 12

When rectangular wave voltage were applied to the compounds obtained in Examples 2, 5, 7 and 9, response times τ(r) and τ for the transitions from the first stable state (dark state), to the third stable state (light state) and from the third stable state (light state) to the second stable state (light state) through the first stable state were measured. τ(r) and τ had preferably the smaller values.

At T−TcA = −10° C, the response times of the compounds obtained in Examples 5, 7, 2 and 9 were compared.

TABLE 2

| Compound | τ(r) μsec | τ μsec |
|---|---|---|
| Compound 5 | 5.4 | 4.4 |
| Compound 7 | 32.4 | 46.4 |
| Compound 2 | 9.2 | 8.4 |
| Compound 9 | 264.0 | 424.0 |

From the results shown in Table 2, it can be said that the compound obtained in Example 5 has a response time one or two figure larger than the compounds obtained in Examples 7 and 9 and nearly two fold larger than the compound obtained in Example 2.

We claim:

1. A liquid crystal compound represented by the formula (I):

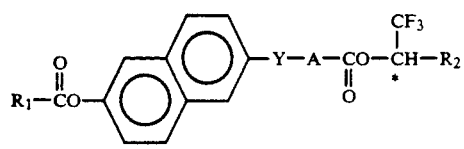

wherein;

R₁ represents an alkyl group having 5-18 carbon atoms,

R₂ represents an alkyl group having 6-16 carbon

Y represents a group

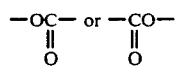

and

A represents

and which exhibits optically tristable states in S*(3) phase.

2. A liquid crystal compound according to claim 1 wherein A represents a group

and Y represents a group $$-\underset{\underset{O}{\|}}{C}O-.$$

3. A liquid crystal compound represented by the following formula:

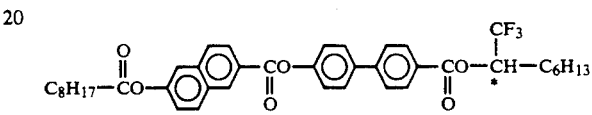

and which exhibits optically tristable states in S*(3) phase.

* * * * *